US006475138B1

United States Patent
Schechter et al.

(10) Patent No.: US 6,475,138 B1
(45) Date of Patent: Nov. 5, 2002

(54) APPARATUS AND METHOD AS PREPARATION FOR PERFORMING A MYRINGOTOMY IN A CHILD'S EAR WITHOUT THE NEED FOR ANAESTHESIA

(75) Inventors: Yossi Schechter, Holon; Martin David Abraham, Hod Hasharon; Giries Kadis, Jaffa; Michael Slatkine, Herzliya, all of (IL)

(73) Assignee: Laser Industries Ltd., Tel Aviv (IL)

( * ) Notice: Subject to any disclaimer, the term of this patent is extended or adjusted under 35 U.S.C. 154(b) by 0 days.

(21) Appl. No.: 09/065,866

(22) Filed: Apr. 24, 1998

Related U.S. Application Data

(63) Continuation-in-part of application No. 08/978,230, filed on Nov. 25, 1997, which is a continuation of application No. 08/501,514, filed on Jul. 12, 1995, now Pat. No. 5,709,627.

(51) Int. Cl.[7] .................................................. A61B 1/22
(52) U.S. Cl. ........................... 600/108; 606/13; 606/17; 600/200
(58) Field of Search ...................... 606/13–19; 600/108, 600/114, 125, 200

(56) References Cited

U.S. PATENT DOCUMENTS 1,106,699 A   8/1914   Carroll (List continued on next page.)

FOREIGN PATENT DOCUMENTS

EP         0172490      5/1986

OTHER PUBLICATIONS

Sharplan 771 Microscan, Mar. 28, 1985, 3 pages.

(List continued on next page.)

*Primary Examiner*—Michael Peffley
(74) *Attorney, Agent, or Firm*—Eitan, Pearl, Latzer & Cohen-Zedek

(57) ABSTRACT

A focusable imaging laser otoscope for performing laser surgery without the need for anesthesia, The apparatus includes a housing, an end member movably disposed within the housing, an imaging device attached to the housing for producing an image of a target area, an illuminating system attached to the housing for illuminating the target area, a speculum having a longitudinal axis and detachably attached to the end member, an optical system attached to the housing and having a main optical axis coaxial with the longitudinal axis of the speculum, for directing a surgical and/or an aiming laser beam from a laser source through the housing and the speculum to strike the target area and for directing image forming light rays to project an image of the target area onto the imaging device such that when the image of the target area is focused, the surgical laser beam and/or aiming laser beam are also focused on the target area, and a focusing assembly attached to the housing and to the end member for adjustably moving the end member and the speculum relative to the housing to focus the image of the target area. The otoscope may also be constructed without a focusing assembly, in which case the speculum may be detachably attached to the housing and the focusing is achieved by selecting an appropriate speculum from an available plurality of specula. The otoscope may also include a sensor system for indicating penetration of the target area. The sensor system may also automatically shut off the surgical laser after penetration of the target area.

63 Claims, 12 Drawing Sheets

U.S. PATENT DOCUMENTS

| | | | |
|---|---|---|---|
| 3,884,236 A | | 5/1975 | Krasnov |
| 4,316,467 A | | 2/1982 | Muckerheide |
| 4,387,952 A | | 6/1983 | Slusher |
| 4,441,485 A | | 4/1984 | Reynolds |
| 4,469,098 A | | 9/1984 | Davi |
| 4,566,453 A | | 1/1986 | Kumano |
| 4,587,396 A | | 5/1986 | Rubin |
| 4,672,969 A | | 6/1987 | Dew |
| 4,712,537 A | * | 12/1987 | Pender .................... 600/200 |
| 4,718,418 A | | 1/1988 | L'Esperance |
| 4,733,660 A | | 3/1988 | Itzkan |
| 4,768,513 A | | 9/1988 | Suzuki |
| 4,913,132 A | | 4/1990 | Gabriel |
| 4,917,083 A | | 4/1990 | Harrington |
| 5,049,147 A | | 9/1991 | Danon |
| 5,057,100 A | * | 10/1991 | Lombardo .................. 606/17 |
| 5,071,417 A | | 12/1991 | Sinofky |
| 5,112,328 A | | 5/1992 | Taboada et al. |
| 5,207,670 A | | 5/1993 | Sinofsky |
| 5,280,378 A | | 1/1994 | Lombardo |
| 5,336,217 A | | 8/1994 | Buys et al. |
| 5,360,424 A | | 11/1994 | Klopotek |
| 5,364,390 A | | 11/1994 | Taboada et al. |
| 5,411,502 A | | 5/1995 | Zair |
| 5,833,683 A | * | 11/1998 | Fuller et al. .................. 606/17 |
| 5,836,939 A | * | 11/1998 | Negus et al. ................. 606/11 |

OTHER PUBLICATIONS

Microprocessor—Controlled Scanning Micromanipulator for Carbon—Dioxide Laser Surgery, J. Neurosurgery 59, Dec. 1983, pp. 1098–1099.

Sharplan 771B Microscan, Lasers Industries (1985).

Sharplan Swiftlase Flashscan, Jun., 1993.

Sharplan Lasers, Inc. Outgoing fax from Karen Amburgey, Oct. 19, 1994.

Reliant Technologies, Inc. Product News,Accu–Scan, Multi–Wavelength Laser Scanning System for CO2, Jan. 25, 1995, 3 pages.

"Aesthetic CO2 Laser System", literature, Aug. 1994, 2 pages.

Mihchael Slatkine, et al. "Instrumentation for Office Laser Surgery", Operative Techniques in Otolaryngology—Head and Neck Surgery, vol. 5, No. 4, Dec. 1994, pp. 211–217.

R. Rox Anderson, et al. "Selective Photothermolysis: Precise Microsurgery by Selective Absorption of Pulsed Radiation", Science, vol. 220, Apr. 29, 1993, pp. 524–527.

Andrew Blitzer, M.D.,DDS "Laser Photocoagulation in the Care of Patients with Osler—Weber—Rendu Disease", Operative Techniques in Otolaryngology—Head and Neck Surgery, vol. 5, No. 4, Dec. 1994, pp. 274–277.

Arielle N.B. Kauvar, et al. "Laser Therapy for Cutaneous Vascular Lesions", Operative Techniques in Otolaryngology—Head and Neck Surgery, vol. 5, No. 4, 1994, pp. 250–258.

Richard W. Maloney, MD "Laser Otology", Operative Techniques in Otolaryngology—Head and Neck Surgery, vol. 3, No. 2, Jun. 1992, pp. 74–83.

I. L. Med. Unilase product info. Brochure "The Proven Solution for Disk, Spinal Cord and Brain Microsurgery" (1993).

I. L. Med. Unilase product info. Brochure "The Proven Solution for Otologic and Microlaryngeal Surgery" (1993).

UNILASE A new CO2 Laser for Microsurgery, I.L. Med. Newsletter, vol. 1, No. 3, Spring 1991.

"New Laser for Microlaryngeal Surgery", I.L. Med. Newsletter, vol. 1, No. 1, Spring 1991.

S. George Lesinski, M.D et al. "Carbon Dioxide Lasers for Otosclerosis", Otolaryngologic Clinics of North America, vol. 26, No. 3, Jun. 1993.

I. L. Med. Unilase System Brochure (1993).

"Using a CO2 Laser During Conventional Microdiskectomy Shows Promise of Faster Recovery", I.L. Med Newsletter, vol. 1. No. 4, Spring 1991.

* cited by examiner

APPARATUS AND METHOD AS PREPARATION FOR PERFORMING A MYRINGOTOMY IN A CHILD'S EAR WITHOUT THE NEED FOR ANAESTHESIA

RELATIONSHIP TO OTHER U.S. PATENT APPLICATIONS

This Application is a continuation in part of U.S. patent application Ser. No. 08/978,230 filed Nov. 25, 1997 which is a continuation of U.S. patent application Ser. No. 08/501,514 filed Jul. 12, 1995, now U.S. Pat. No. 5,709,677.

FIELD OF THE INVENTION

The present invention relates generally to laser devices and biomedical applications thereof. More specifically, the invention relates to setting-up a laser-based system in preparation for performing a myringotomy in an ear without the need for anaesthesia.

BACKGROUND OF THE INVENTION

Myringotomy is a widely-performed procedure used in the treatment of "Otitis Media"-acute inflammation of the middle ear. Typically, it involves a surgical procedure whereby the surgeon performs a tiny incision of the eardrum in order to enable the drainage of fluids that accumulate in the eardrum. The incision in the eardrum must remain open and thus an open drainage ring is placed in the incision to prevent rapid healing and occlusion of the incision. This surgery is done under general anaesthesia.

Over the last few years surgeons performed myringotomy surgery using a pulsed $CO_2$ laser. The advantage of the pulsed $CO_2$ laser is its generation of thermal heat resulting in delayed healing of the incision of the eardrum. The incision remains open for approximately 3–6 weeks without the aid of an open drainage ring. Both the incision diameter and laser pulse time duration affect the incision healing time. Typically, the incision diameter is approximately 1 mm and the laser pulse time duration is 0.1 second at a 3–5 Watt power. This surgical technique is generally performed under anaesthesia, because the surgery uses a "defocused" beam that does not account for a child's unexpected movement.

There is a need to perform the myringotomy procedure more accurately without the need for anaesthesia. Moreover, there is a need to perform the myringotomy on the tympanic membrane of the child's ear drum such that any sudden, unexpected movement of the child's head will not adversely affect the carrying out of the myringotomy. The present invention, as described as follows, provides such an improved myringotomy procedure in children without anaesthesia.

A common problem in systems having an optical imaging system for providing a focusable image of a target using while also providing a laser directing optical system for directing a surgical and or aiming laser beam at the same target is that the co-focusing action usually involves a system for coordinating the moving of at least some optical components of both the imaging optical system and the laser directing optical system. Such coordinated movement mechanisms are expensive, difficult to construct and maintain and may frequently become un-coordinated.

There is thus a need for hand held otoscope for myringotomy and other applications which has a simple optical system which does not require coordinated moving of different optical components while still enabling the user to focus an aiming laser beam and monitor the focusing and aiming action thereof on a display prior to activating the surgical laser beam. The present invention, as described as follows, provides an improved myringotomy device for use in performing myringotomy in children and adults without anesthesia.

SUMMARY OF THE INVENTION

One aspect of the invention relates to a method and apparatus suitable for carrying out laser surgery, such as for performing a myringotomy without the need for anaesthesia. The apparatus includes focusable imaging laser otoscope having a single focusing mechanism which enables focusing both the imaging optics and the laser focusing optics without requiring coordinated moving of the imaging optical components and the laser focusing optical components, enabling the user to focus an aiming laser beam and monitor the focusing and aiming action thereof on a display prior to activating the surgical laser beam.

Another aspect of the present invention is a sensor attached within the apparatus for sensing electromagnetic radiation emissions emanating from the target area in response to the surgical laser beam or the aiming laser beam striking the target area and for indicating the penetration of the target area.

Yet another aspect of the present invention is a system including a sensor attached within the apparatus, and a processing unit connected to the sensor and to the surgical laser. The sensor senses electromagnetic radiation emissions emanating from the target area in response to the surgical laser beam or the aiming laser beam striking the target area. The sensor produces a signal which is processed by the processing unit for automatically detecting the penetration of the target area. The processor unit controls the surgical laser and automatically stops the lasing of the surgical laser upon detecting the penetration of the target area.

There is therefore provided, in accordance with a preferred embodiment of the present invention, an apparatus for performing laser surgery without the need for anesthesia. The apparatus includes a housing, an end member movably disposed within the housing, an imaging device attached to the housing for producing an image of a target area, an illuminating system attached to the housing for illuminating the target area. The apparatus further includes a speculum having a longitudinal axis, a first end and a second end. The second end of the speculum detachably attached to the end member. The apparatus further includes an optical system attached to the housing and having a main optical axis coaxial with the longitudinal axis of the speculum, for directing a surgical and/or an aiming laser beam from a laser source through the housing and the speculum to strike the target area, and for directing image forming light rays to project an image of the target area onto the imaging device such that when the image of the target area is focused, the surgical laser beam and/or aiming laser beam are also focused on the target area. The apparatus further includes a focusing assembly attached to the housing and to the end member for adjustably moving the end member and the speculum relative to the housing to focus the image of the target area.

There is also provided, in accordance with a preferred embodiment of the present invention, an apparatus for performing laser surgery without the need for anesthesia. The apparatus includes a housing having an end, an imaging device attached to the housing for producing an image of a target area, an illuminating system attached to the housing for illuminating the target area. The apparatus also includes a speculum having a longitudinal axis, a first end and a second end. The second end of the speculum is detachably attached to the end of the housing. The apparatus also includes an optical system attached to the housing and having a main optical axis coaxial with the longitudinal axis of the speculum, for directing a surgical and/or an aiming laser beam from a laser source through the housing and the speculum to strike the target area and for directing image forming light rays to project an image of the target area onto the imaging device such that when the image of the target area is focused, the surgical laser beam and/or aiming laser beam are also focused on the target area.

Furthermore, in accordance with another preferred embodiment of the present invention, the speculum is exchangeable with any selected one of a plurality of specula, each one of the plurality of specula having different dimensions. The image of the target area is focused by selecting a suitable speculum out of the plurality of specula.

Furthermore, in accordance with another preferred embodiment of the present invention, the laser source is connected to the housing through a scanner for scanning the surgical laser beam and/or the aiming laser beam along a portion of the target area.

Furthermore, in accordance with another preferred embodiment of the r present invention, the scanner is a flashscanner or a silktouch scanner.

Furthermore, in accordance with another preferred embodiment of the present invention, the laser source includes a pulsed or a continuous laser.

Furthermore, in accordance with another preferred embodiment of the present invention, the laser source further includes an aiming laser.

Furthermore, in accordance with another preferred embodiment of the present invention, the laser source includes a surgical laser coupled to the optical system by an optical fiber.

Furthermore, in accordance with another preferred embodiment of the present invention, the surgical laser is a pulsed laser or a continuous wave laser.

Furthermore, in accordance with another preferred embodiment of the present invention, the surgical laser is selected from a pulsed $CO_2$ laser, a continuous $CO_2$ laser and an erbium laser.

Furthermore, in accordance with another preferred embodiment of the present invention, the aiming laser beam is produced by an aiming laser source attached within the housing. The aiming laser source includes an aiming laser and coupling optics for combining the aiming laser beam with the surgical laser beam. The optical system includes a dichroic beam combiner for combining the surgical laser beam and/or the aiming laser beam with the image forming light rays.

Furthermore, in accordance with another preferred embodiment of the present invention, the illuminating system includes a non coherent light source coupled to an optical fiber bundle for providing an illuminating beam directed towards the target area.

Furthermore, in accordance with another preferred embodiment of the present invention, the optical system includes a dichroic beam combiner and a beam splitter for combining the surgical laser beam and/or the aiming laser beam with viewing rays directed by the optical system towards the imaging device and with the illuminating beam.

Furthermore, in accordance with another preferred embodiment of the present invention, the illuminating system includes a non coherent light source, an illuminating member attached to the housing and an optical fiber bundle. The optical fiber bundle has a first end optically coupled to the non-coherent light source and a second end disposed within the illuminating member to provide an annular illuminating system at an end of the illuminating member facing the target area.

Furthermore, in accordance with another preferred embodiment of the present invention, the aiming laser beam is produced by an aiming laser source attached within the housing.

Furthermore, in accordance with another preferred embodiment of the present invention, the aiming laser source includes an aiming laser and coupling optics for combining the aiming laser beam with the surgical laser beam.

Furthermore, in accordance with another preferred embodiment of the present invention, the aiming laser is a diode laser.

Furthermore, in accordance with another preferred embodiment of the present invention, the imaging device is a charge coupled device or a video camera.

Furthermore, in accordance with another preferred embodiment of the present invention, the apparatus further includes a display device for displaying the image of the target area to a user.

Furthermore, in accordance with another preferred embodiment of the present invention, the surgical laser beam has a power level and reflects of the desired target area. The apparatus further includes a sensor arranged in a path traveled by the reflected surgical laser beam the sensor detects changes in the power level reflected off the desired target area, the sensor indicating when the power level being reflected is such that the penetration of the desired target area has occurred.

Furthermore, in accordance with another preferred embodiment of the present invention, electromagnetic radiation emissions emanate from the target area in response to the surgical laser beam or the aiming laser beam striking the target area and the apparatus further includes a sensor arranged in a path traveled by the electromagnetic radiation emissions, the sensor detects changes in the electromagnetic radiation emissions from the target area, the sensor indicating when the electromagnetic emissions are such that penetration of the target area has occurred.

Furthermore, in accordance with another preferred embodiment of the present invention, the surgical laser beam has a power level and reflects of the target area. The apparatus further includes a sensor arranged in a path traveled by the reflected surgical laser beam. The sensor detects changes in the power level reflected off the target area. The sensor indicates when the power level being reflected is such that the penetration of the target area has occurred.

Furthermore, in accordance with another preferred embodiment of the present invention, electromagnetic radiation emissions emanate from the target area in response to the surgical laser beam or the aiming laser beam striking the target area. The apparatus further includes a sensor arranged in a path traveled by the electromagnetic radiation emissions. The sensor detects changes in the electromagnetic radiation emissions from the target area. The sensor indicates when the electromagnetic radiation emissions are such that the penetration of the target area has occurred.

Furthermore, in accordance with another preferred embodiment of the present invention, the sensor is connected to a processing unit. The processing unit is connected to the laser source for controlling the operation thereof. The processing unit determines from signals produced by the sensor whether penetration of the target has occurred. The processing unit automatically shuts off the surgical laser beam after penetration of the target has occurred.

There is further provided, in accordance with another preferred embodiment of the present invention, an apparatus for performing laser surgery without the need for anesthesia. The apparatus includes a housing, an imaging device attached to the housing for producing an image of a target area, and an illuminating system attached to the housing for illuminating the target area. The apparatus also includes a speculum having a longitudinal axis, a first end and a second end. The second end of the speculum is detachably and movably attached to the housing. The apparatus also includes an optical system attached to the housing and having a main optical axis coaxial with the longitudinal axis of the speculum, for directing a surgical and/or an aiming laser beam from a laser source through the housing and the speculum to strike the target area and for directing image forming light rays to project an image of the target area onto the imaging device, such that when the image of the target area is focused, the surgical laser beam and/or aiming laser beam are also focused on the target area. The apparatus further includes a focusing mechanism attached to the speculum for adjustably moving the speculum relative to the housing along the main optical axis to focus the image of the target area.

There is also provided, in accordance with another preferred embodiment of the present invention, a method for performing laser myringotomy without the need for anesthesia, using a focusable imaging laser otoscope. The otoscope includes a housing, a speculum movable with respect to the housing and an illuminating system attached to the housing. The otoscope further includes a surgical laser source and an aiming laser source connected to the housing, an optical system, and an imaging device attached to the housing for imaging a target area. The otoscope is connected to a display which is connected to the imaging device. The method includes the steps of inserting the speculum into the opening of an ear, displaying an image indicative of the target area on the display, focusing the image of the target area on the display by moving the speculum relative to the housing, directing an aiming laser beam produced by the aiming laser source towards a desired portion of the target area suitable for performing laser surgery, to form an illuminated aiming spot on the desired portion, the spot being visible within the image displayed on the display, adjusting the position of the spot on the desired portion of the target area by suitably moving the otoscope within the ear, and firing a surgical laser beam produced by the surgical laser source towards the desired portion of the target area.

There is further provided, in accordance with another preferred embodiment of the present invention, a method for performing laser myringotomy without the need for anesthesia, using an imaging laser otoscope. The otoscope includes a housing, a speculum detachably attached to the housing, and an illuminating system attached to the housing. The otoscope further includes a surgical laser source and an aiming laser source connected to the housing. The otoscope further includes an optical system and an imaging device attached to the housing for imaging a target area. The otoscope is connected to a display which is connected to the imaging device. The method includes the steps of selecting the speculum from a plurality of specula having different dimensions, attaching the speculum to the housing, inserting the speculum into the opening of an ear, displaying an image indicative of the target area on the display, focusing the image of the target area on the display by moving the speculum within the ear, directing an aiming laser beam produced by the aiming laser source towards a desired portion of the target area suitable for performing laser surgery to form an illuminated aiming spot on the desired portion, the spot is visible within the image displayed on the display, adjusting the position of the spot on the desired portion of the target area by suitably moving the otoscope within the ear, and firing a surgical laser beam produced by the surgical laser source towards the desired portion of the target area.

Furthermore, in accordance with another preferred embodiment of the present invention, the target area is the tympanic membrane of the eardrum of the ear and the image is indicative of the tympanic membrane.

Furthermore, in accordance with another preferred embodiment of the present invention, the surgical laser beam has a power level and reflects of the desired portion. The otoscope further includes a sensor arranged in a path traveled by the reflected surgical laser beam. The sensor detects changes in the power level reflected off the desired portion. The method further includes the step of indicating when the power level being reflected is such that the penetration of the desired portion of the target area has occurred.

Furthermore, in accordance with another preferred embodiment of the present invention, electromagnetic radiation emissions emanate from the desired portion of the target area in response to the surgical laser beam or the aiming laser beam striking the desired portion. The apparatus further includes a sensor arranged in a path traveled by the electromagnetic radiation emissions. The sensor detects changes in the electromagnetic radiation emissions from the desired portion. The method further includes the step of indicating when the electromagnetic radiation emissions are such that the penetration of the desired portion of the target area has occurred.

Furthermore, in accordance with another preferred embodiment of the present invention, the sensor is connected to a processing unit. The processing unit is connected to the surgical laser source for controlling the operation thereof. The method further includes, after the step of firing a surgical laser beam, the steps of the processing unit determining from signals produced by the sensor whether penetration of the target has occurred, and automatically shutting off the surgical laser beam by the processing unit after penetration of the target has occurred.

BRIEF DESCRIPTION OF THE DRAWINGS

For a better understanding of the present invention, reference is made to the following description and accompanying drawings, in which like components are designated by like reference numerals, while the scope of the invention is set forth in the appended claims.

DESCRIPTION OF THE PREFERRED EMBODIMENT

Figure 1:
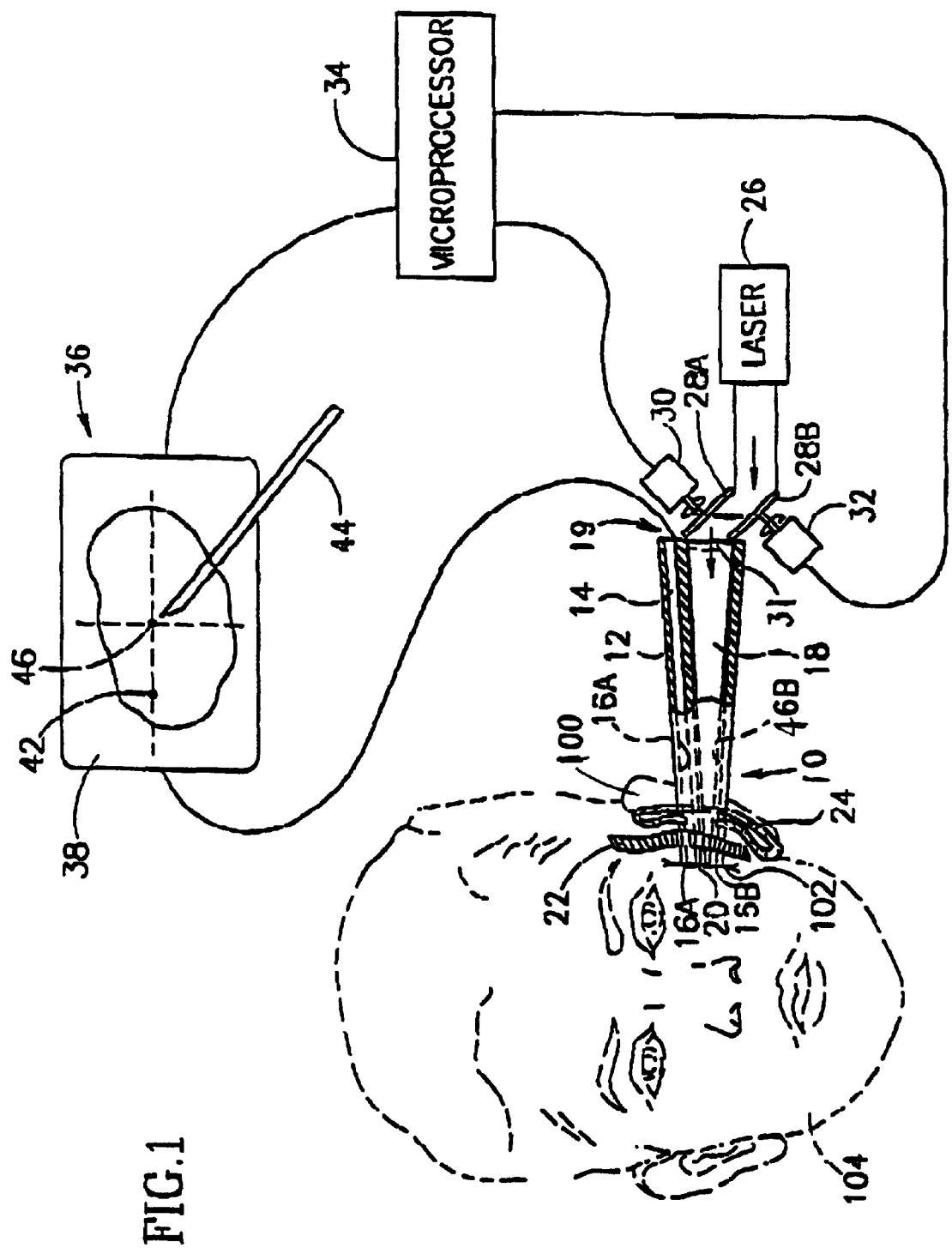
FIG. 1 is a schematic representation of the layout for performing myringotomy in children with a micromanipulator adhered to a child's head in accordance with the invention.

FIG. 1 shows a micromanipulator 10, which is a type of small, rigid, operating otoscope. It has a housing 12 that has through-going channels 16A, 16B. A viewing device 14 is within the channel 16A and rigidly affixed to the housing 12. A laser beam 18 emerges from a lens 31 in an exit region 19 to pass through the other channel 16B. This exit region 19 neighbors the entrance to this other channel 16B.

The housing 12 has a forward end 20, which is preferably open or transparent to permit viewing and lasing therethrough. The housing 12 is inserted into the patient's ear 100 so that the forward end 20 faces the ear drum 102. An adhesive strip 22 adheres the housing 12 to the patient's head 104 and a band 24 is wrapped around the ear in the manner shown in FIG. 1. The housing thus moves in unison with the patient's head and thereby with the tympanic membrane area to be lased.

A movable scanner mirror 28A is rotatable about one axis in response to actuation of a control motor 30 and as movable scanner mirror 28B is movable about another axis perpendicular to the one axis in response to actuation of another control motor 32. These motors 30, 32 are selectively actuated to rotate the mirrors 28A, 28B into a desired orientation and stopped in response to instructions from a microprocessor 34.

A video monitor 36 with a viewing screen 38 displays the image 40 of a tympanic membrane of the ear drum. The image 40 arises from signals transmitted from the viewing device 14. In the image 40, the current striking location 42 of the laser beam may become visible to assist the physician in determining from where the striking position is to be moved.

One way to make the current striking location 42 visible in the image 40 is to fire a visible laser beam at the location where firing the laser for performing the laser surgery is to strike. This could be done with a pilot laser appropriately positioned to fire such a beam.

Another way to make the current striking location 42 visible in the image 40 is to observe the changes in infrared temperature emissions on the tympanic membrane of a short burst of the invisible laser beam that is to be used to perform the laser surgery. The burst preferably is of shorter duration than and not as strong as the laser bursts used for the laser surgery, but sufficient for a noticeable impact on the image of the tympanic membrane on the viewing screen.

An electronic pen pointer 44 is used to mark a target location 46 on the screen 38 that corresponds to a target area to be lased as determined by a physician or other medical personnel by contacting the viewing screen 38 accordingly. Either the screen 38 or electronic pen pointer 44 is responsive to such contact to provide coordinate information of this target location 46 to the microprocessor 34.

The current striking location 42 must become known to the microprocessor 34 to effect the appropriate calculations for instructing the mirror control motors 30, 32 to move and rotate the scanner mirror 28 accordingly. This could be done by sending the microprocessor 34 coordinate information on the current striking location 42 in response to the physician using the electronic pen pointer 44 to contact the viewing screen 38 at the current striking location 42 as it appears in the image 40. Of course, the microprocessor 42 will need to be programmed to detect whether the physician is marking location 42 or target location 46. The program may be such that coordinate information relating to location 42 always precedes that relating to the target location 46 and the physician could be so prompted through an appropriate message on the viewing screen 38.

As an alternative, the microprocessor may ascertain the current striking location 42 on its own based on the relative position of the scanner mirror 18 or on previously determined coordinate information stored in memory that represent the current striking location. In this manner, the physician need only mark the target location 46 corresponding to where the surgery is to be performed.

After making such a comparison of coordinate information as between locations 42 and 46, the microprocessor 24 instructs the mirror control motors 30, 32 to rotate the scanner mirrors 28A, 28B to the appropriate relative orientation. Thus, upon firing of the laser 26 thereafter, the beam 18 that is emitted strikes the scanner mirror 28, which in turn deflects the beam in dependence upon the screen's relative angular inclination to the desired target area on the tympanic membrane that corresponds to that of the target location 46 in the image 40.

Figure 2:
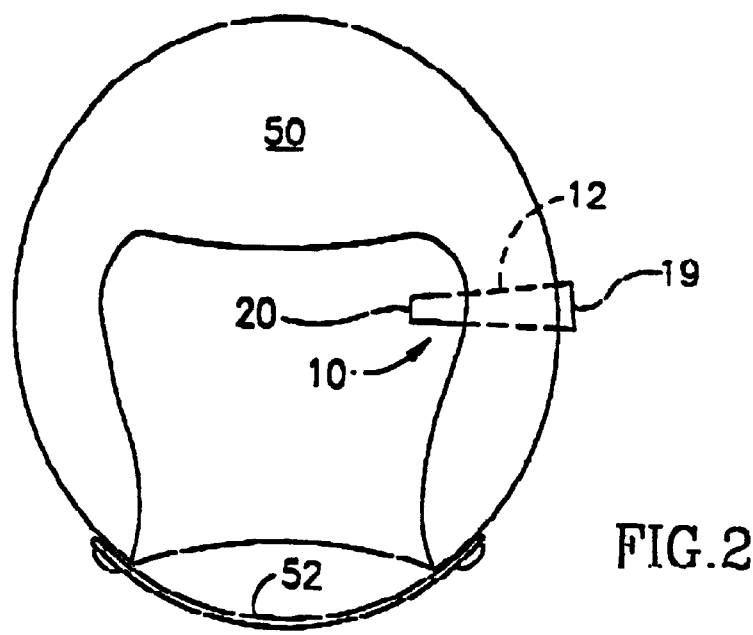
FIG. 2 is a schematic representation of the micromanipulator of FIG. 1 except that it is within a helmet.

FIG. 2 shows a helmet 50 used to retain the micromanipulator 10 in position on the patient's head. The forward end 20 of the micromanipulator is positioned to face the tympanic membrane of the ear drum as was the case in FIG. 1. If the micromanipulator 10 must be inserted further into the ear itself after the helmet is put on, this may be done manually by the physician while viewing the insertion on the viewing screen 38. The helmet may have a passage that defines the channels 16A, 16B of the housing 12; in effect, the helmet could be the housing itself.

If the patient could be injured if the helmet is removed while the micromanipulator 10 extends into the ear, then safety precautions can be taken to prevent this from happening. For instance, the fastening and unfastening of a chin strap 52 could trigger whether the micromanipulator can be inserted into the ear (i.e., only if the chin strap is fastened) or the immediate withdrawal of the micromanipulator 10 under spring bias (i.e., if the chin strap is unfastened).

Figure 3:
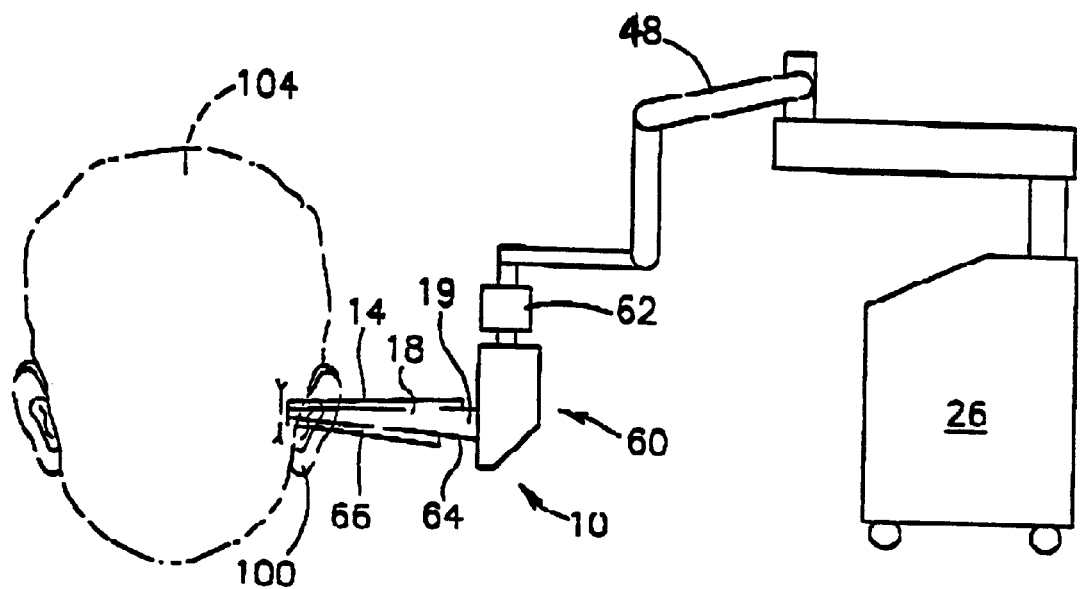
FIG. 3 is a laser apparatus suited for use in accordance with the invention of FIGS. 1 or 2.

Referring to FIG. 3, the articulated arm 48, which is between the laser 26 and the micromanipulator 10, is jointed to permit the micromanipulator 10 to be moved relative to the laser 26. The articulated arm 48 is constructed in a conventional manner, such as is disclosed in U.S. Pat. No. 5,411,502 (the '502 patent), entitled SYSTEM FOR CAUSING ABLATION OF IRRADIATED MATERIAL OF LIVING TISSUE WHILE NOT CAUSING DAMAGE BELOW A PREDETERMINED DEPTH, issued to Eliezer Zair on May 2, 1995, which is incorporated herein by reference. The arm 48 may be hollow to allow extension therethrough of fiber cable, wave guides or other laser transmitting media to convey the laser beam emitted from the laser 26 to the micromanipulator 10. Thus, sudden, unexpected movements of the head 104 will be compensated by the articulated arm 48 moving in conjunction with the micromanipulator 10 and thereby with movement of the head.

The micromanipulator 10 may include a joystick 60 to enable the surgeon to manipulate the viewing device within the housing 12 as desired. The scanner mirror 28 and mirror control motors 30, 32 of FIG. 1 may be within enclosures 62. For the sake of brevity, the viewing screen 38 and the microprocessor 34 of FIG. 1 are not shown in FIG. 3, but they may be remote from or attached to the unit shown in FIG. 3.

Also, the common housing 12 of FIG. 1 is not shown and could be omitted; instead, the viewing device 14 could be rigidly attached, e.g., with an adhesive, to a handpiece 64 through which passes the laser beam 18 in the manner shown in FIG. 3. The handpiece 64 could be inserted into the channel 16B of the housing 12 of the embodiment of FIGS. 1 and 2.

The entire treatment is performed independent of child head movement. If the child's head happens to move when the laser is being aimed or fired, the movement will not necessitate manual re-aiming as was done conventionally because the micromanipulator moves with the movement of the child's head. In addition, the treatment should not be much longer or more annoying for the patient (child), who conventionally is diagnosed with an otoscope without anesthesia. The healing time should be about six weeks.

The individual components mentioned are conventional, except for the shape of the housing 12. The housing may be made from any nonreflective material to avoid creating deflections of the beam passing through its chamber 16B. The length of the chamber 16B should be of a sufficient length to allow the beam to reach the target area with a desired spot size. The chamber may be configured to facilitate attaining the desired dimension. The viewing device 14 is exemplified by a charge coupled device or television camera.

The video monitor 36 is conventional, but any conventional viewing screen such a flat screen, projection screen, etc. may be used as an alternative, preferably passing coordinate information to the microprocessor 34 as desired. If the screen is touch sensitive, the physician could simply touch the screen at the appropriate target location and coordinate information would be generated and processed by the microprocessor 34.

Any conventional marking technique for sending coordinate information to the microprocessor may be used instead of the electronic pen pointer. For instance, a keyboard terminal or other data entry device such as a mouse, joystick or track ball could be used that move a cursor to the appropriate location on a monitor screen. Alternatively, a light emitting pointer device could be used where the monitor screen is photosensitive. These types of devices may be considered marking devices since they are used to identify or mark a location on a screen. Once such a location is marked, coordinate information is transmitted to the microprocessor for further processing.

In addition, the marking device (e.g., the electronic pen pointer 44) and the microprocessor 34 may be dispensed with entirely. For instance, by observing the image 40 on the viewing screen 38 alone, the observer can see the current striking location 42. By moving a joystick 60 (see FIG. 3), which is connected to allow manipulation of the laser beam (in the manner taught in the '502 patent or the Sharplan 710 micromanipulator), the aiming of the laser beam and thereby the current striking location 42 can be moved to the target location 46 that corresponds to the desired target area in the tympanic membrane to be lased. Such movement of the current striking location 42 is watched on the viewing screen 38. Once the current striking location 42 reaches the target location 46, the laser 26 may be fired to commence the laser surgery on the corresponding target area.

One suitable type of laser 26 is a $CO_2$ laser emitting a defocused beam. Preferably, the spot size is 1 millimeter and the power level is 5 watts with a time duration of 0.1 seconds. Another suitable type is a Nd:YAG laser with a pulsed energy of ½ joule, with the same 1 millimeter spot size and fired for one or two pulses. Still another suitable type of laser 26 employs a flashscanner, such as that of a Sharplan 710 micromanipulator, to provide better control of the hole diameter since the beam emitted is focused, preferably making a spiral pattern as it scans the target area.

Examples of laser disclosures suitable for making a spiral pattern and/or a lissageous pattern to serve as the laser 26 of the present application: the '502 patent and U.S. Pat. No. 5,582,752, entitled "METHOD AND APPARATUS FOR APPLYING A LASER BEAM TO A WORKING SURFACE, PARTICULARLY FOR ABLATING TISSUE", which are incorporated herein by reference.

While carrying out the laser surgery, it may be medically important to know when the tympanic membrane has been penetrated. As soon as this is known, the lasing process can cease to save the posterior section of the middle ear from unnecessary laser radiation (although the laser beam is expected to be unfocussed and not damaging).

Upon observation of the image 40 as seen on the viewing screen 38, the physician can watch the lasing of the hole through the membrane to know when the tympanic membrane of the ear drum has been penetrated to permit the escape of excess fluid. When such penetration arises, there will be a noticeable change in the observed characteristics at the target area as it appears on the viewing screen 38.

For instance, infrared temperature emissions from the target area in the tympanic membrane from use of the surgical laser beam vary depending upon whether the tympanic membrane has been penetrated or not. If a visible pilot laser beam is used to check the hole penetration, such as that from a He—Ne pilot laser, the reflected power level of the beam varies depending upon whether the tympanic membrane has been penetrated or not. In either case, penetration is readily observed on the viewing screen 38.

As an alternative to observing for changes to check penetration, a sensor 66 (see FIG. 3) may be used which, when it senses penetration of the tympanic membrane, shuts off the laser automatically. For instance, a sensor of reflected power level could be used where a He—Ne pilot laser is fired at the hole penetration. A sensor of infrared radiation emissions could be used where a laser suited for performing the laser surgery is fired at the hole penetration.

In accordance with the preferred embodiment, the beam positioning device or scanner may include the scanner mirror 28, the mirror control motors 30, 32 and the exit region 19. In addition, the beam positioning device may further include the microprocessor 34, marking device and transmission of coordinate information from the viewing screen 38.

The mirror control motors 30, 32 may be any other form of drivers for the scanner mirrors 28A, 28B, whether driven electrically, pneumatically or hydraulically. The microprocessor 34 may instead be any other type of controller that performs the same functions and may be in the form of other integrated circuitry or its analog counterpart.

The present invention is advantageously used on children because securing the housing to the child's head ensures that the housing moves in unison with movements of the child's head instead of independent of it.

Figure 4:
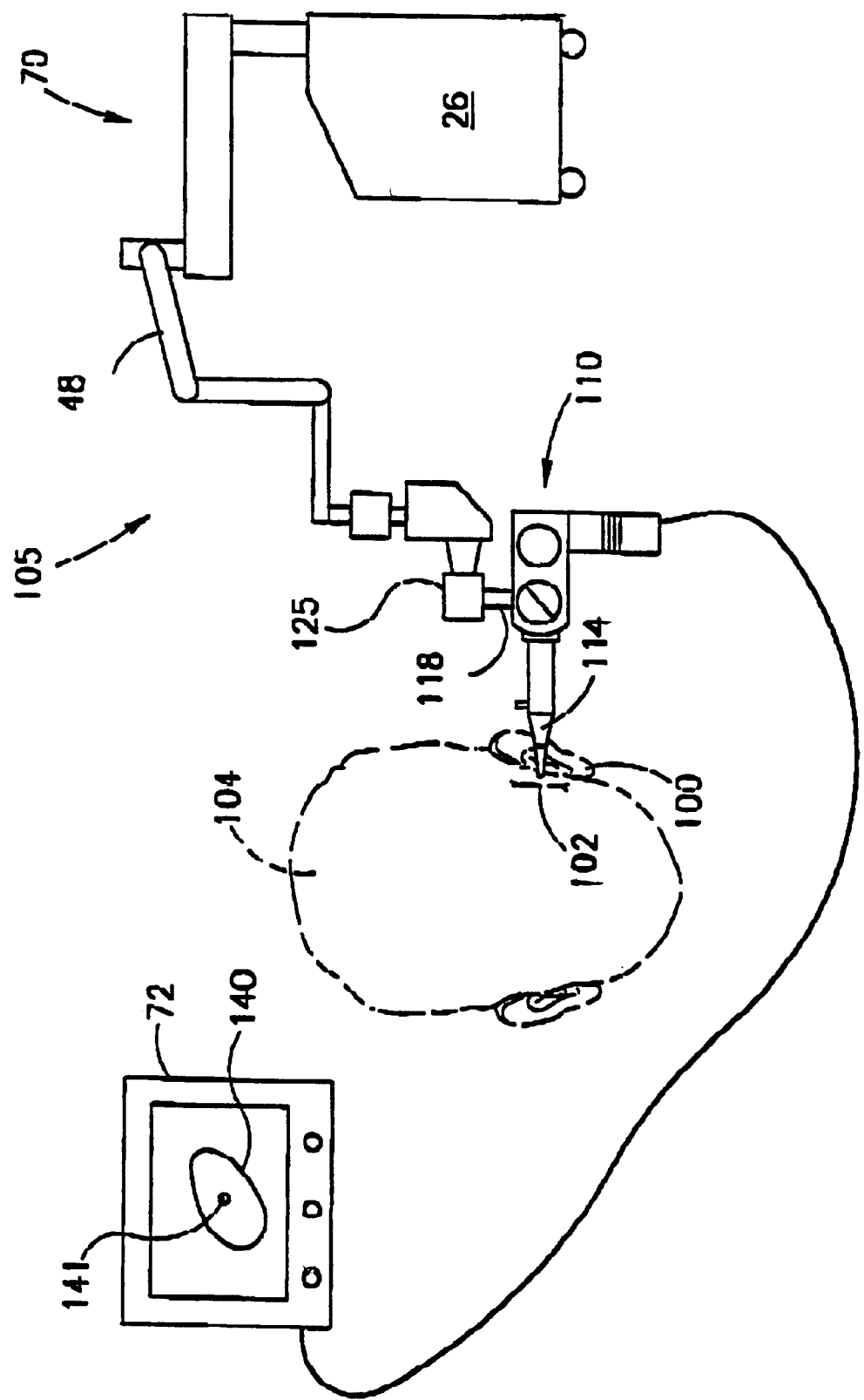
FIG. 4 is a schematic representation of a system for performing myringotomy with a focusable imaging laser otoscope, in accordance with a preferred embodiment of the present invention.

Reference in now made to FIGS. 4–7. FIG. 4 is a schematic representation of a system for performing myringotomy with a focusable imaging laser otoscope, in accordance with a preferred embodiment of the present invention. The focusable imaging laser otoscope of FIG. 4 is a type of small, hand held operating otoscope. The system 105 includes a focusable otoscope 110 which is connected to a laser source 70 and to a display 72. The laser source 70 includes a laser 26 coupled to the otoscope 110 by an articulated arm 48 which is optically coupled to a scanner 125.

The articulated arm 48 is constructed in a conventional manner, such as is disclosed in U.S. Pat. No. 5,411,502 (the '502 patent), entitled SYSTEM FOR CAUSING ABLATION OF IRRADIATED MATERIAL OF LIVING TISSUE WHILE NOT CAUSING DAMAGE BELOW A PREDETERMINED DEPTH, issued to Eliezer Zair on May 2, 1995, which is incorporated herein by reference. The arm 48 may be hollow to allow extension therethrough of fiber cable, wave guides or other laser transmitting media to convey the laser beam emitted from the laser 26 to the otoscope 110. Thus, sudden, unexpected movements of the head and of the ear 100 of the patient 104, into which the otoscope 110 is inserted during the performance of the myringotomy procedure, will be compensated by the articulated arm 48 moving in conjunction with the otoscope 110 and thereby with movement of the head.

The otoscope 110 is optically coupled to the scanner 125 by an optical coupler 118. The scanner 125 can be any suitable scanner device. One suitable type of laser 26 is a $CO_2$ laser emitting a defocused beam. Preferably, the spot size is 1 millimeter and the power level is 5 watts with a time duration of 0.1 seconds. Another suitable type is an Nd:YAG laser with a pulsed energy of ½ joule, with the same 1 millimeter spot size and fired for one or two pulses. Still another suitable type of laser 26 is a flashscanner, such as that of a Sharplan 710 micromanipulator, to provide better control of the hole diameter since the beam emitted is focused, preferably making a spiral pattern as it scans the target area.

Examples of laser disclosures suitable for making a spiral pattern and/or a lissageous pattern to serve as the laser 26 of the present application: the '502 patent and U.S. Pat. No. 5,582,752, entitled "METHOD AND APPARATUS FOR APPLYING A LASER BEAM TO A WORKING SURFACE, PARTICULARLY FOR ABLATING TISSUE", which are incorporated herein by reference. The otoscope 110 is suitably connected to a display 72 for displaying an image provided by the otoscope 110. The image 140 is representative of a target area such as the tympanic membrane of the eardrum 102 of the patient's ear 100. The otoscope 110 includes a speculum 114 detachably attached thereto which can be inserted into the ear 100.

Figure 5:
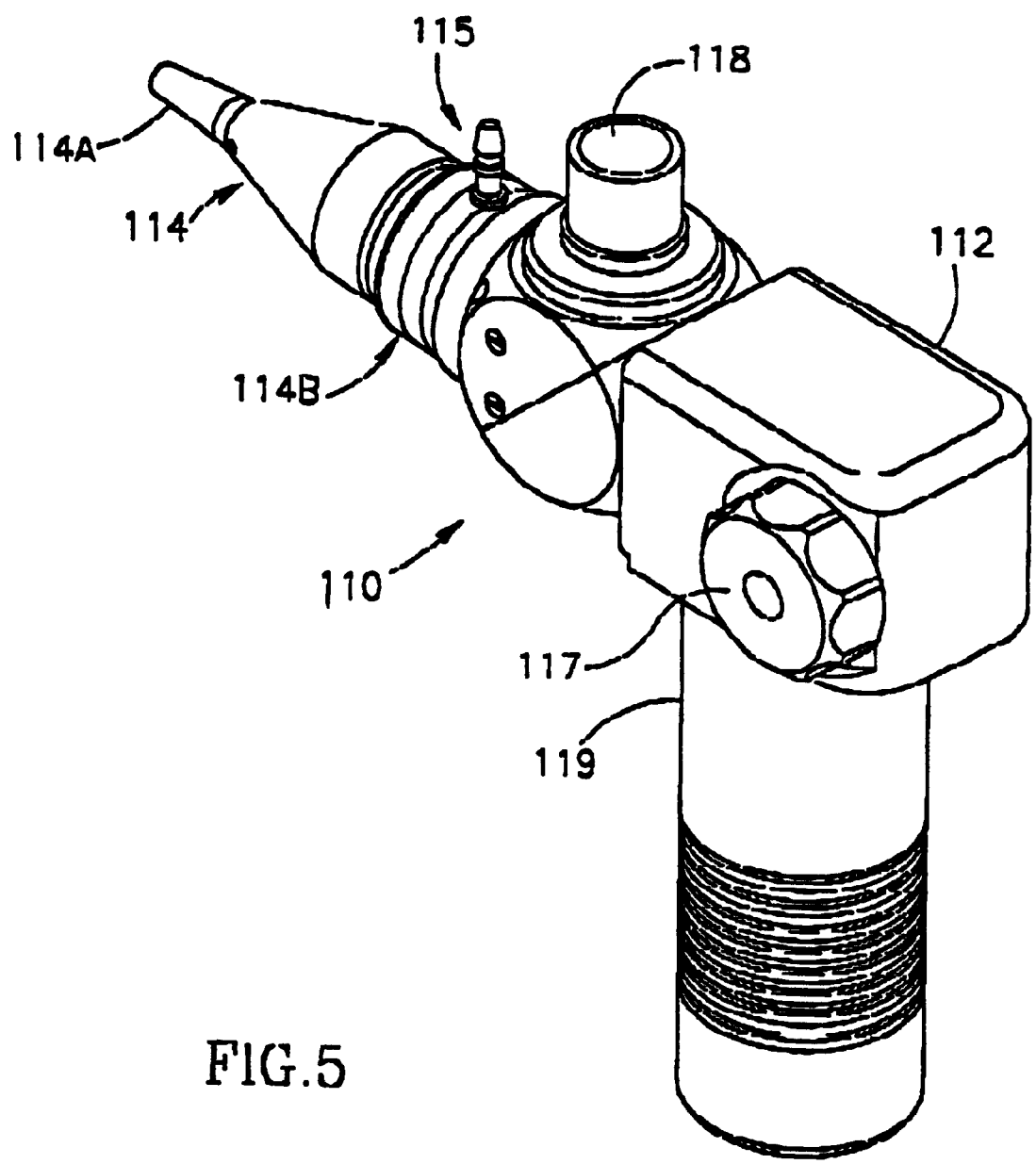
FIG. 5 is a schematic isometric view illustrating the focusable imaging laser otoscope of FIG. 4 in detail.

Reference is now made to FIG. 5 which is a schematic isometric view illustrating the focusable imaging laser otoscope of FIG. 4 in detail. The otoscope 110 includes a housing 112 having a handle 119. The otoscope 110 further includes a speculum 114 having a first end 114A and a second end 114B. The second end 114B is detachably attached to the otoscope 110. The physician using the otoscope 110 holds the handle 119 in his hand to suitably direct it and inserts the end 114A into the ear 100. The otoscope 110 further includes a focusing knob 117 for adjustably moving the speculum 114 with respect to the housing 112 as disclosed in detail hereinafter. The otoscope 110 further includes a venting nipple 115 for venting smoke and vapors created during the perforation of the tympanic membrane 102 by the surgical laser beam. The nipple 115 may be connected during surgery to a vacuum pump (not shown) for venting smoke and vapors from the speculum 114 and from the ear canal.

Figure 6:
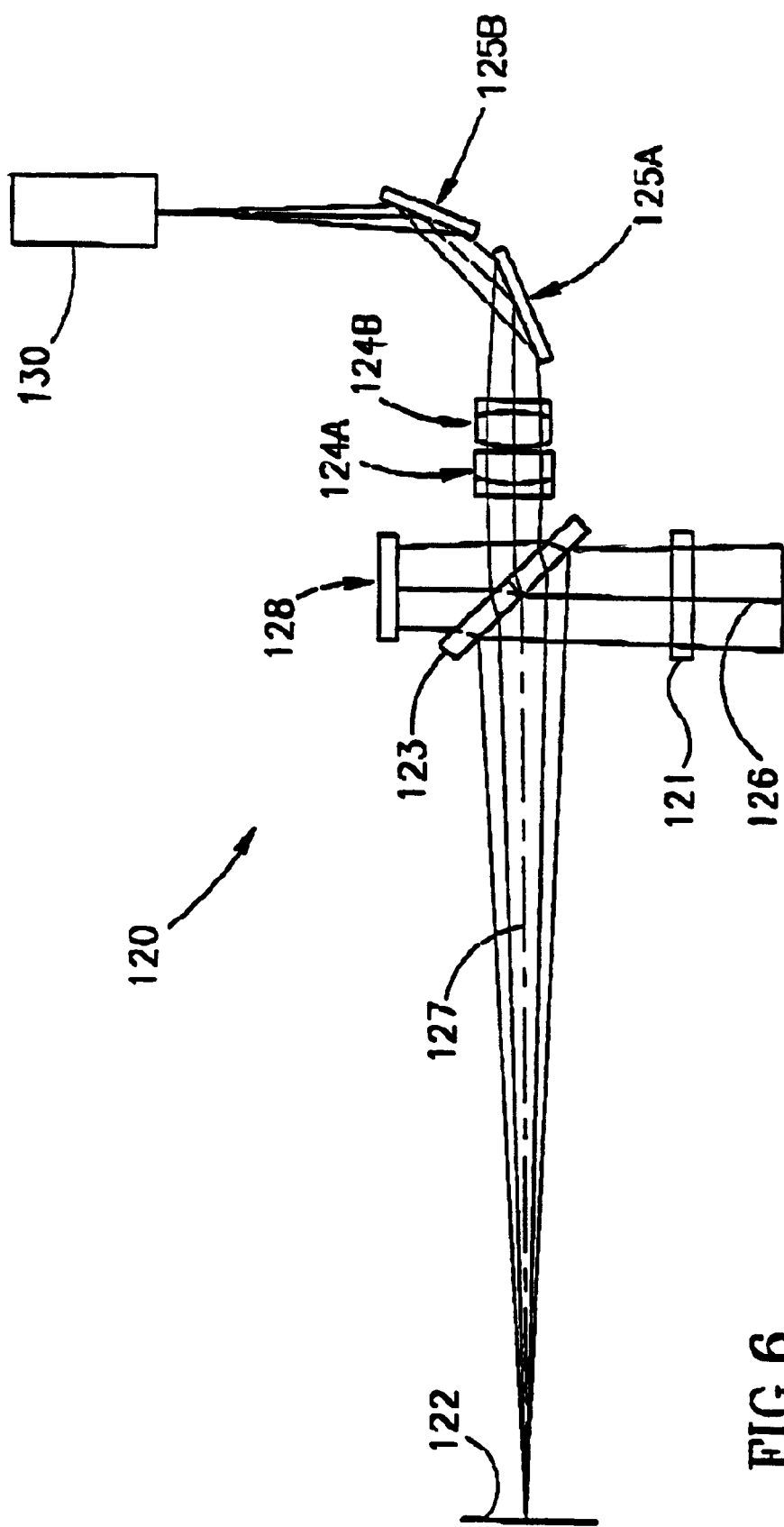
FIG. 6 is a schematic diagram of an optical system disposed within the otoscope of FIG. 5.

Reference is now made to FIG. 6 which is a schematic diagram of an optical system 120 disposed within the otoscope 110 of FIG. 5. The optical system 120 includes an imaging device 130 such as a charge coupled device (CCD), a video camera or any other suitable imaging device. Imaging light rays coming from an illuminating system (not shown) are reflected from a target (not shown) at the working plane 122 of the otoscope 110 to pass through a dichroic beam combiner 123 and a pair of relay lenses 124A and 124B, and are folded by folding mirrors 125A and 125B onto the imaging device 130. The illuminating system is disclosed in detail hereinafter.

The optical system 120 has a main optical axis 127. A surgical laser beam exiting the scanner 125 (FIG. 4) along the path 126 enters the optical system 120 through the optical coupler 118 (not shown in FIG. 6), passes through a lens 121, is reflected by the dichroic beam combiner 123 and is focused at the working plane 122. Similarly, a visible aiming laser beam (not shown) exiting the scanner 125 will travel a similar path to be focused at the working plane 122. The size and the position of the spot irradiated by the surgical laser beam and the aiming laser beam is identical. Thus, the size and position of the spot 141 (FIG. 4) appearing on the image 140 representing the target area, serves as an indicator of the position and size of the spot that will be created by the activation of the surgical laser beam. The dichroic beam combiner 123 serves to combine the Infra-red surgical laser beams with the visible aiming laser beam and the polychromatic imaging rays of the illuminating system (not shown).

A light absorber 128 absorbs stray light from the aiming laser beam, to prevent the light from flooding of the imaging device 130.

It is noted that, while all the optical components of the system 120 are shown as being coplanar (for the sake of clarity of illustration), the different optical components can be disposed within the housing 112 in a non coplanar arrangement by suitably adapting the folding mirrors or other optical components.

Figure 7:
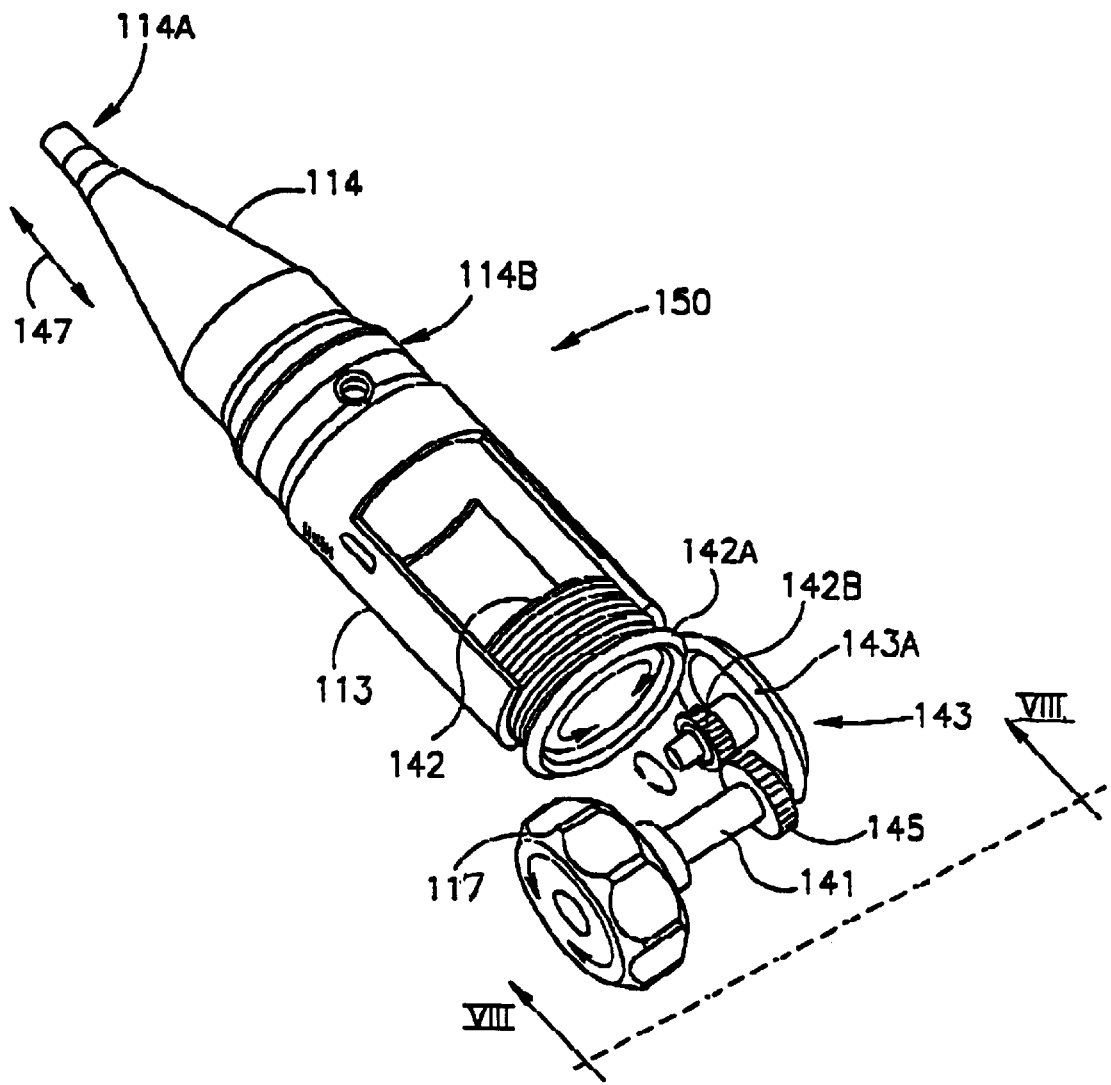
FIG. 7 is a schematic part isometric part cutaway view illustrating the focusing assembly of the otoscope of FIG. 5 in detail.
Figure 8:
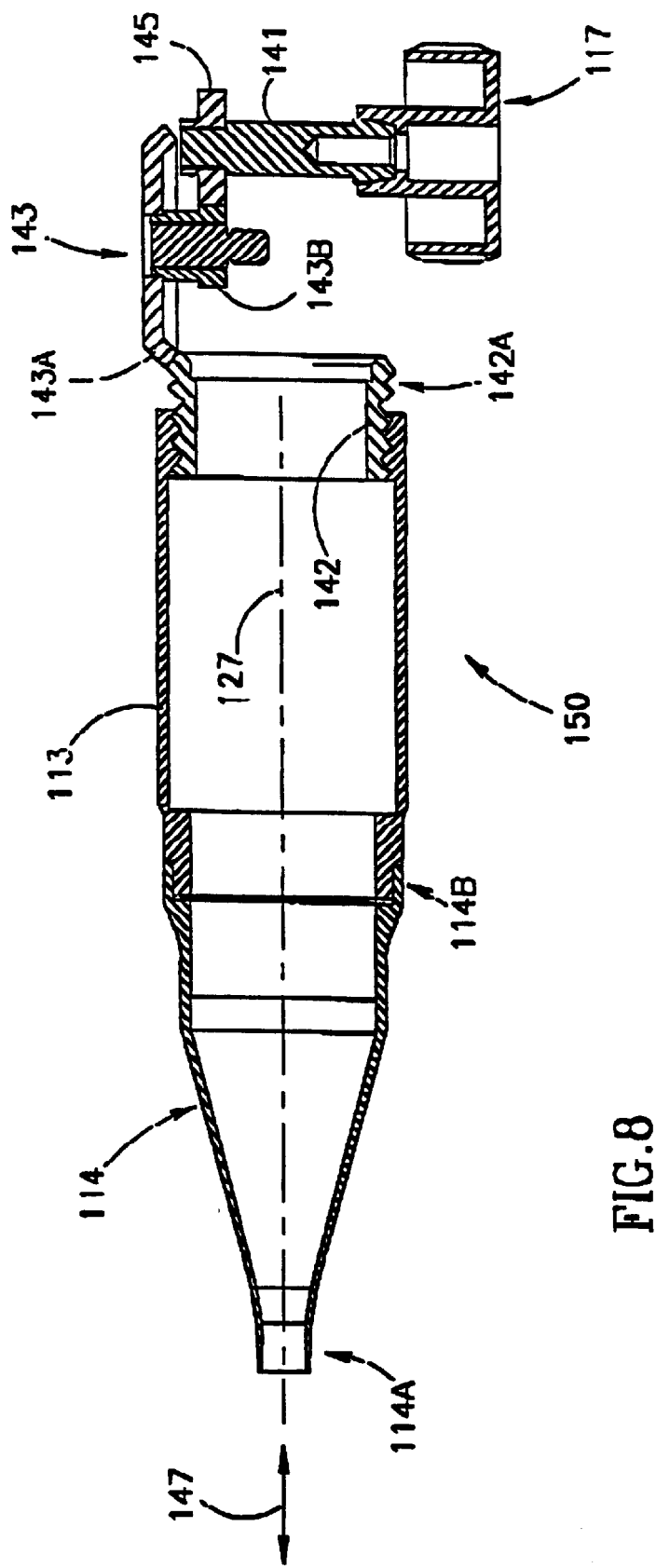
FIG. 8 is a schematic cross section of the focusing assembly of FIG. 7 taken along the lines VIII—VIII.

Reference is now made to FIGS. 7 and 8. FIG. 7 is a schematic part isometric part cutaway illustrating the focusing assembly of the otoscope of FIG. 5 in detail. FIG. 8 is a schematic cross section of the focusing assembly of FIG. 7 along the lines VIII—VIII.

The focusing assembly 150 is attached to a movable end member 113 movably disposed within the housing 112 (not shown). The end member 113 is a cylindrical hollow member can be moved with respect to the housing 112 along the directions represented by the double headed arrow 147. It is noted that, FIGS. 7 and 8 also show the speculum 114 attached to the end member 113. The second end 114B of the speculum 114 is detachably attached to the end member 113.

The focusing assembly 150 includes a rotatable externally threaded member 142 having a beveled end 142A. The end member 113 is internally threaded and is movably engaged with the rotatable threaded member 142. The focusing assembly 150 further includes a gear member 143 rotatably attached to the housing 112 (not shown). The gear member 143 includes a beveled gear 143A and a spur gear 143B rigidly attached to the beveled gear 143A. The beveled end 142A is rotatably engaged with the beveled gear 143A. The focusing assembly 150 further includes a focusing knob 117 rotatably attached to the housing 112 (not shown). The focusing knob 117 is rigidly coupled to a spur gear 145 by a shaft 141. The spur gear 145 is engaged with the spur gear 143B. When the focusing knob 117 is rotated clockwise or counterclockwise, the end member moves away from or towards the focusing knob 117, respectively, along the main optical axis 127 of the optical system 120.

The arrangement of the focusing assembly 150 relative to the optical system 120 enables focusing the image 140 representing the target area on the display 72 by rotating the focusing knob 117. The optical system 120 is factory pre-calibrated such that when the image 140 of the target area is focused on the display, both the surgical laser beam and the aiming laser beam will be focused at the target area which is generally co-planar with the working plane 122 (FIG. 6).

The disclosed mechanical arrangement has the advantage of obviating the need for a complicated and expensive mechanism for simultaneously moving the imaging optics and the optics for focusing the surgical and aiming laser beams in a coordinated fashion that would have been required if the speculum 114 would have been rigidly attached to the housing 112 of the otoscope 110.

Thus, in accordance with a preferred embodiment of the present invention, the movable speculum 114 is moved relative to the housing 112 to which the optical system 120 is rigidly attached, instead of moving the various components of the optical system 120.

Figure 9:
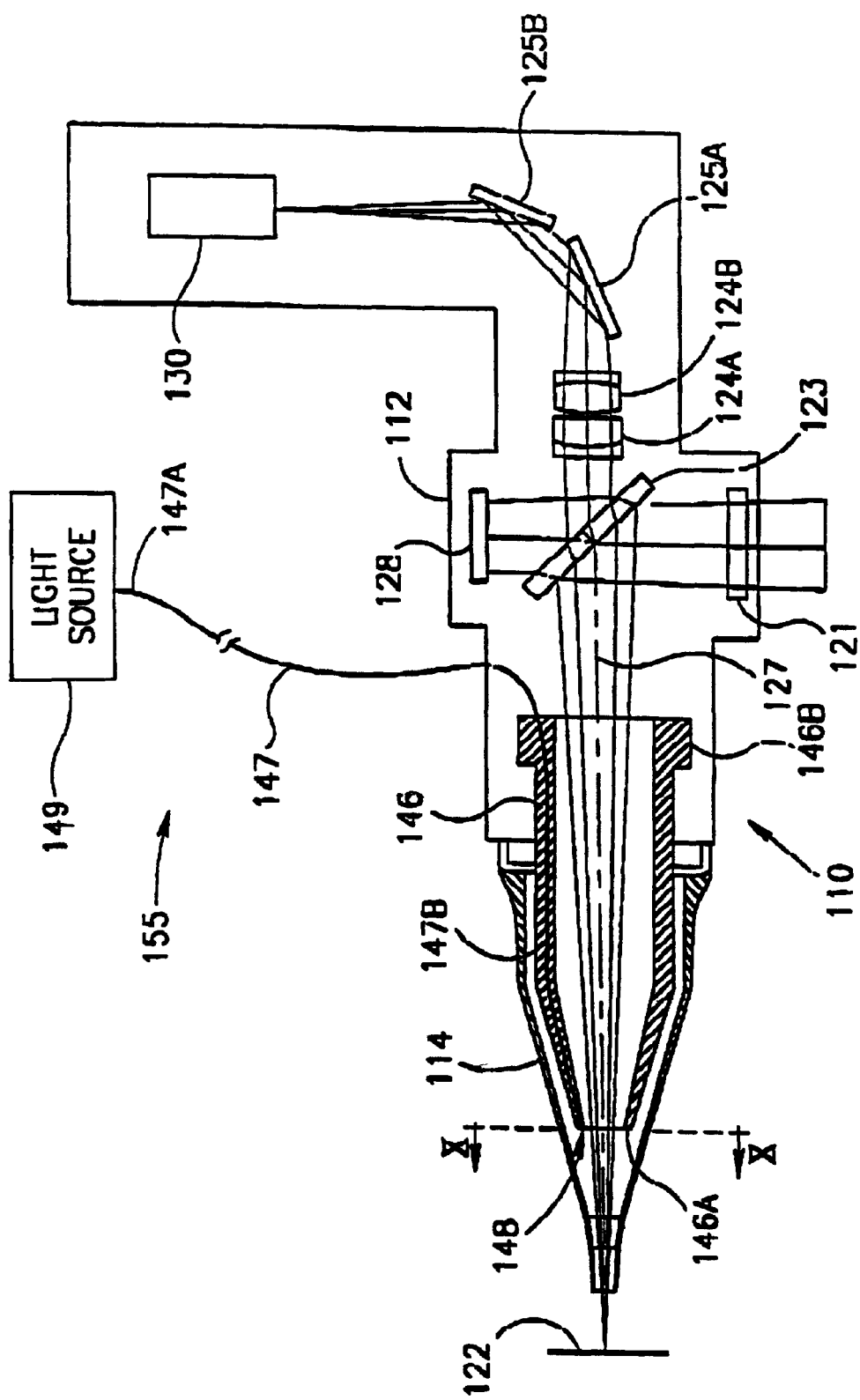
FIG. 9 is a schematic diagram illustrating the layout of an illuminating system of the otoscope of FIG. 5 in detail.
Figure 10:
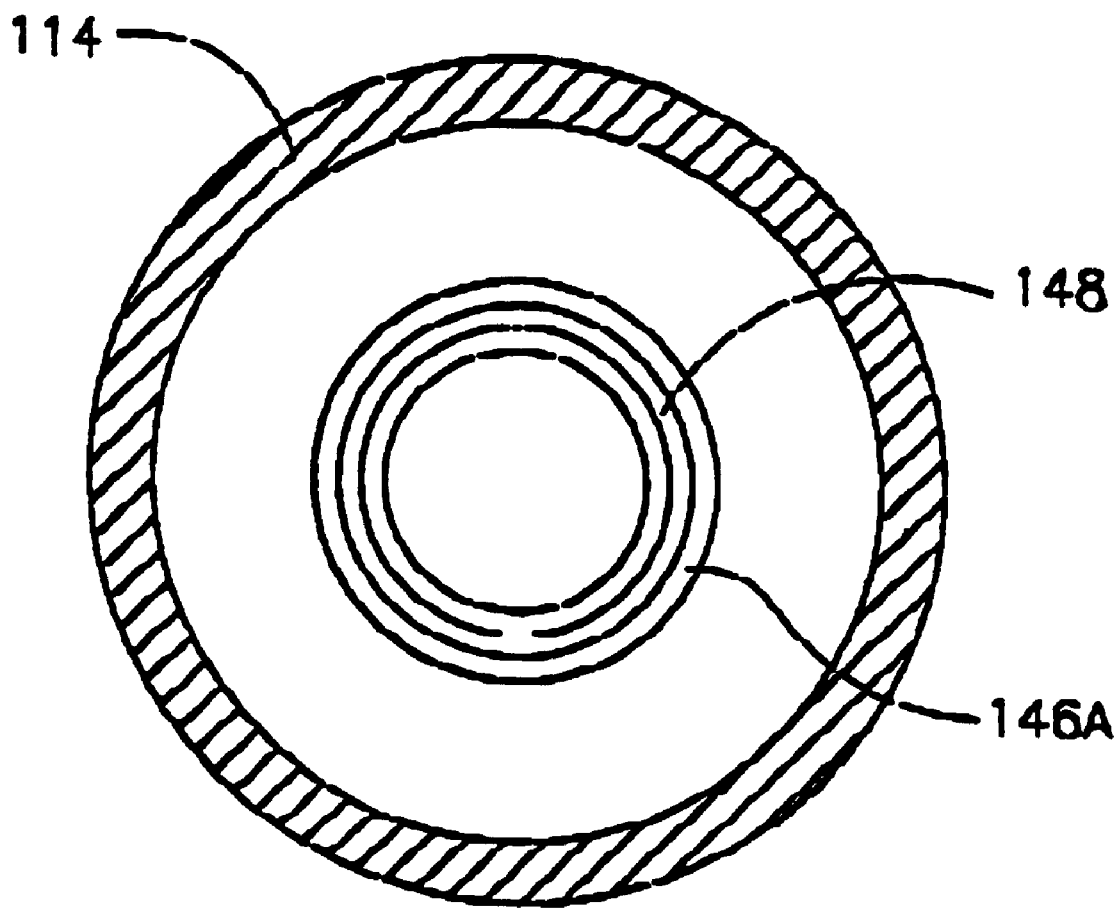
FIG. 10 is a schematic cross section of the otoscope of FIG. 9 taken along the lines X—X.

Reference is now made to FIGS. 9 and 10. FIG. 9 is a diagram schematically illustrating the layout of illuminating system of the otoscope of FIG. 5. FIG. 10 is a cross section of the otoscope of FIG. 9 taken along the lines X—X.

The illuminating system 155 of the otoscope 110 includes an illuminating member 146 disposed within the end member 113 (not shown) and rigidly attached within the housing 112, an incoherent light source 149 and an optical fiber bundle 147. The illuminating member has a first end 146A disposed within the speculum 114 and a second end 146B disposed within the end member 113. The fiber bundle 147 has two ends, a first end 147A is optically coupled to the light source 149 and a second end 147B which is disposed within the illuminating member 146. The second end 147B terminates at the surface of the end 146A of the illuminating member 146 to form an annular illuminating source 148. The annular illuminating source 148 provides light for illuminating the target area positioned at the working plane 122, and the light rays which are reflected from the target area are the image forming light rays which are directed towards the imaging device 130 by the optical system 120 (FIG. 6).

It is noted that, the illuminating system 155 of the otoscope 110 of FIG. 9 which is independent on the optical system 120 can also be implemented in a different way.

Figure 11:
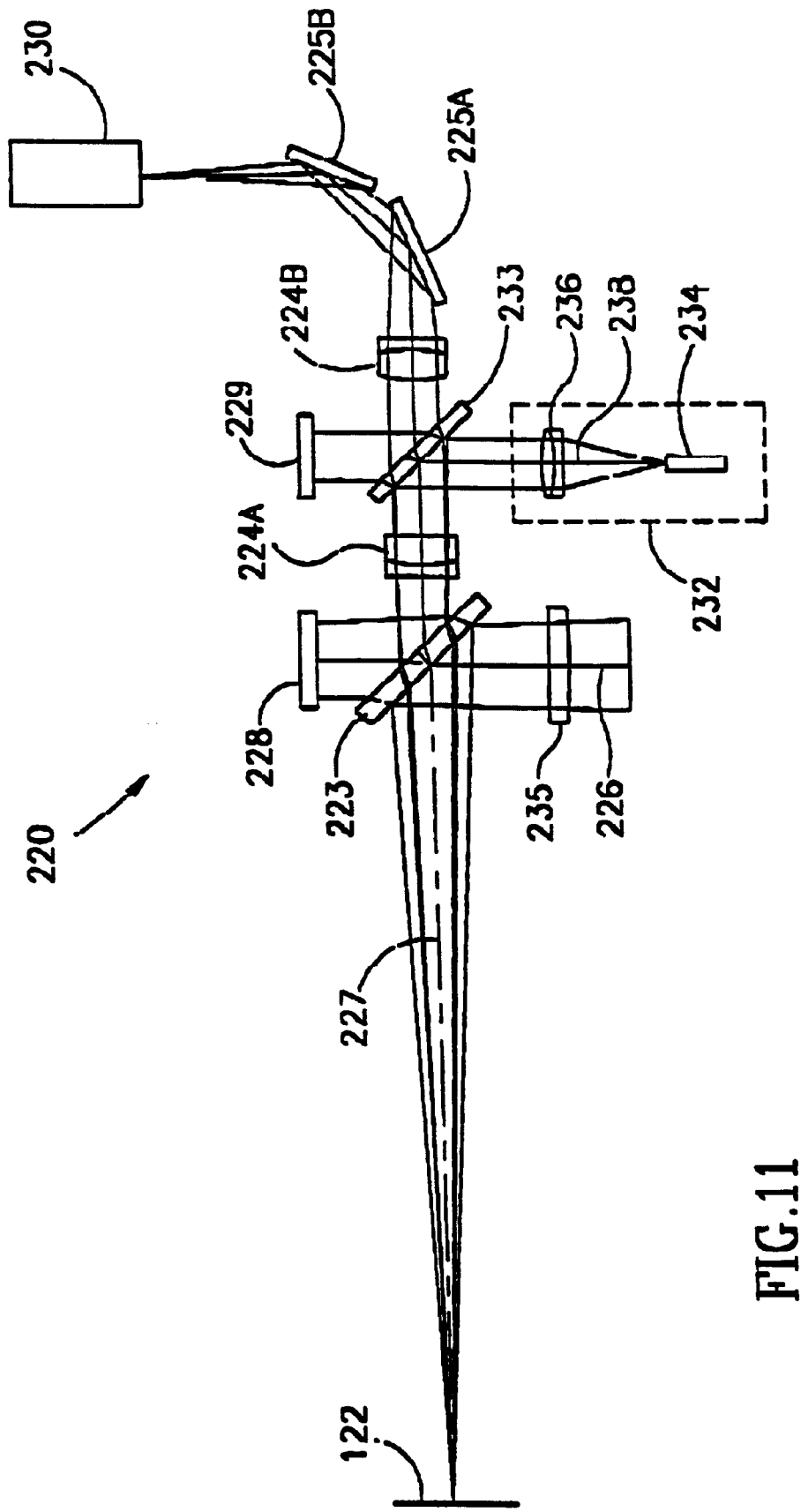
FIG. 11 is a schematic cross sectional diagram illustrating the layout of an optical system for a different implementation of an otoscope, in accordance with another preferred embodiment of the present invention.

Reference is now made to FIG. 11 which is a schematic cross sectional diagram illustrating the layout of an optical system for a different implementation of an otoscope, in accordance with another preferred embodiment of the present invention.

The optical system 220 includes an imaging device 230 such as a charge coupled device (CCD), a video camera or any other suitable imaging device.

The optical system 220 further includes an illuminating system 232. The illuminating system 232 includes an illuminating source such as an optical fiber bundle 234 and a condenser lens 236. The fiber bundle 234 is optically coupled to a light source (not shown) which is preferably a broad band non-coherent light source but can also be any other suitable coherent or non-coherent light source. Imaging light rays 238 coming from the fiber bundle 234 are collimated by the condenser lens 236 and are reflected from a 50/50 beam splitter 233 to pass through a relay lens 224A, and a dichroic beam combiner 223 which then directs the rays 238 to a target area (not shown) positioned at the working plane 122. The rays are then reflected from the target at the working plane 122 and pass through the dichroic beam combiner 123, the relay lens 224A, the 50/50 beam splitter 233 and a relay lens 124B and are finally folded by folding mirrors 225A and 225B onto the imaging device 230. Thus, in contrast with the optical system 120 of FIG. 6 in which the illuminating rays directly illuminate the target, the illuminating light rays of the illuminating system 232 pass through some optical components of the optical system 220 before illuminating the target area on the working plane 122.

The optical system 220 further include a stray light absorber 229 for absorbing stray light from the illuminating source 232 which passes through the beam splitter 233.

The optical system 220 has a main optical axis 227. A surgical laser beam exiting the scanner 125 (FIG. 4) along the path 226 enters the optical system 220 through the optical coupler 118 (not shown in FIG. 11), passes through a lens 235, is reflected by the dichroic beam combiner 223 and is focused at the working plane 122. Similarly, a visible aiming laser beam (not shown) exiting the scanner 125 will travel a similar path to be focused at the working plane 122. The size and the position of the spot irradiated by the surgical laser beam and the aiming laser beam is identical. Thus, the size and position of the spot 141 (FIG. 4) appearing on the image 140 representing the target area, serves as an indicator of the position and size of the spot that will be created. The dichroic beam combiner 223 serves to combine the Infra-red surgical laser beams with the visible aiming laser beam and the polychromatic imaging rays of the illuminating system 232.

A light absorber 228 absorbs stray light from the aiming laser beam, to prevent the light from flooding of the imaging device 230.

It is noted that, while all the optical components of the system 220 are shown as being coplanar (for the sake of clarity of illustration), the different optical components can be disposed within the housing 112 in a non coplanar arrangement by suitably adapting the folding mirrors or other optical components.

It is further noted that, while the preferred embodiments illustrated in FIGS. 6 and 11 use a scanner (FIG. 7) for directing the surgical laser beam and the aiming laser beam towards the target area, other implementations of the otoscope are also possible in which the surgical laser beam is differently delivered from a surgical laser coupled to an optical fiber. In a non-limiting example the surgical laser is a CO2 laser coupled to an optical fiber and the aiming laser is a diode laser.

Figure 12:
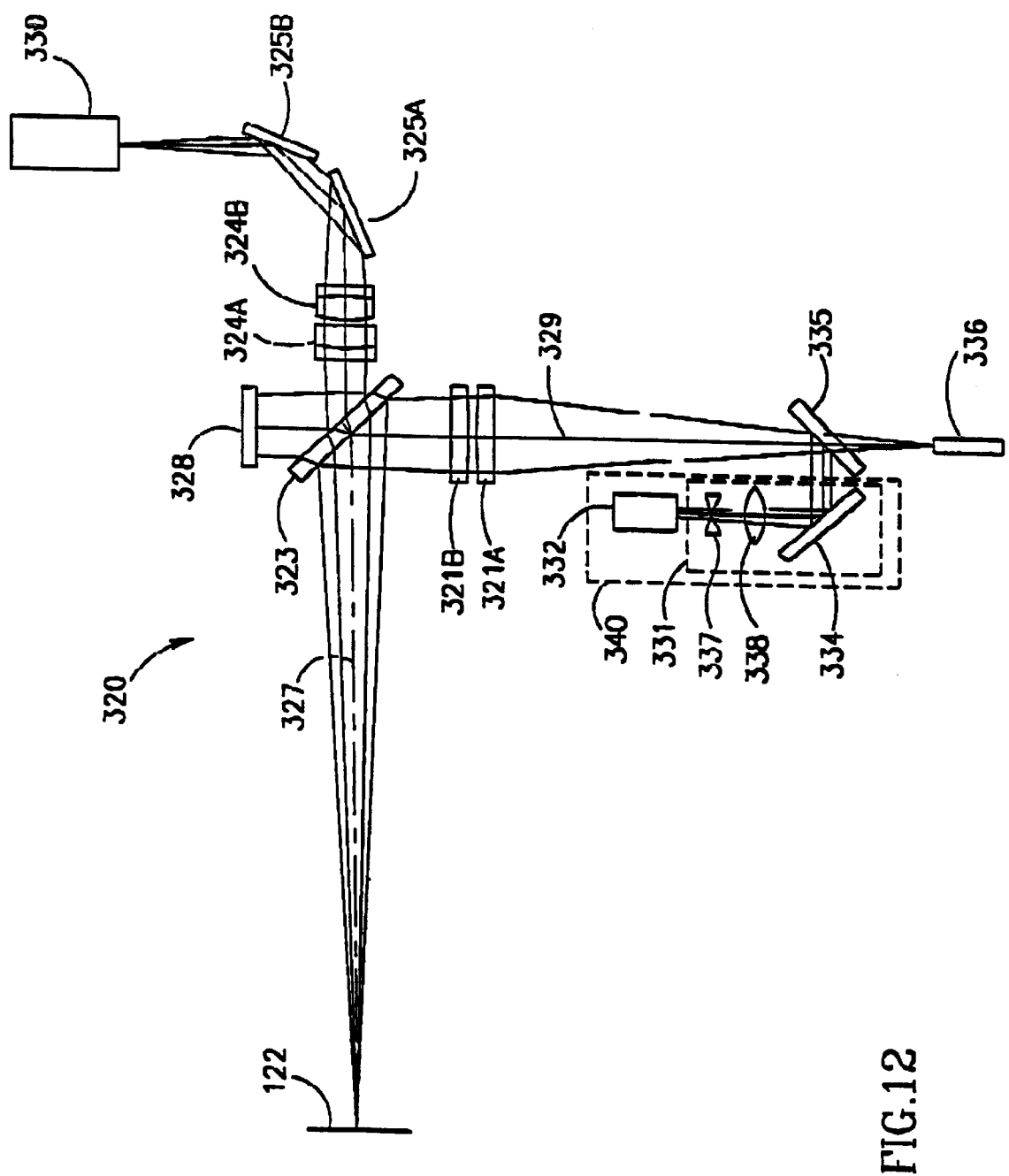
FIG. 12 is a schematic cross sectional diagram illustrating the layout of an optical system for yet another implementation of an otoscope including a fiber coupled surgical laser and a diode aiming laser, in accordance with another preferred embodiment of the present invention.

Reference is now made to FIG. 12 which is a schematic cross sectional diagram illustrating the layout of an optical system for yet another implementation of an otoscope including a fiber coupled $CO_2$ surgical laser and a diode aiming laser, in accordance with another preferred embodiment of the present invention.

The optical system 320 includes an imaging device 330 such as a charge coupled device (CCD), a video camera or any other suitable imaging device. Imaging light rays coming from an illuminating system such as the illuminating system 155 of FIG. 9, are reflected from a target (not shown) at the working plane 122 to pass through a dichroic beam combiner 323 and a pair of relay lenses 324A and 324B, and are folded by folding mirrors 325A and 325B onto the imaging device 330. A suitable illuminating system is the illuminating system 155 (not shown in FIG. 12) as disclosed in detail hereinabove (FIGS. 9 and 10). However, it is noted that, other suitable illuminating systems known in the art may also be used for illuminating the target area.

The optical system 320 has a main optical axis 327. A surgical laser beam exits from an optical fiber 336, suitably coupled to a surgically suitable $CO_2$ laser. The laser beam passes along the path 329 through a beam combiner 335 and is collimated by fiber relay lenses 321A and 321B. The beam is then reflected by a dichroic beam combiner 323 and is focused at the working plane 122.

The optical system 320 further includes an aiming laser source 340. Generally, when using an optical fiber coupled to a surgical $CO_2$ laser, a separate aiming laser source is needed because the optical fiber normally used in conjunction with infra-red surgical $CO_2$ lasers is not optically suitable for transmitting visible light. The aiming laser source 340 includes an aiming laser 332 and coupling optics 331. The coupling optics 331 include lenses 337 and 338 and a folding mirror 334. The coupling optics 331 are designed in such a way that the aiming laser beam and the surgical laser beam focus at the working plane 122 with nearly identical spot diameters. In a non-limiting example, the aiming laser 332 is a diode laser such as an SDL3038-033 diode laser commercially available from Sanyo Corporation, Japan.

The visible aiming laser beam (not shown) exiting the aiming laser 332 is directed by the coupling optics 331 and folded by the folding mirror 334 towards the beam combiner 335 which reflects it towards the fiber relay lenses 321A and 321B. After passing through the fiber relay lenses 321A and 321B, the aiming laser beam is reflected from the dichroic beam combiner 323 towards the target area within the working plane 122.

Thus, the size and position of the spot 141 (FIG. 4) appearing on the image 140 representing the target area, serves as an indicator of the position and size of the spot that will be created by the activation of the surgical laser beam.

The dichroic beam combiner 123 serves to combine the Infra-red surgical laser beams with the visible aiming laser beam and the polychromatic imaging rays of the illuminating system (not shown).

A light absorber 328 absorbs stray light from the aiming laser beam, to prevent the light from flooding of the imaging device 330.

It is noted that, while all the optical components of the system 320 are shown as being coplanar (for the sake of clarity of illustration), the different optical components can be disposed within the housing 112 in a non coplanar arrangement by suitably adapting the folding mirrors or other optical components.

It is also noted that, while the otoscopes disclosed hereinabove enable the physician to focus the aiming and surgical laser beams by using the focusing knob 117, it is also possible to use alternative implementations which do not include a focusing assembly.

Figure 13:
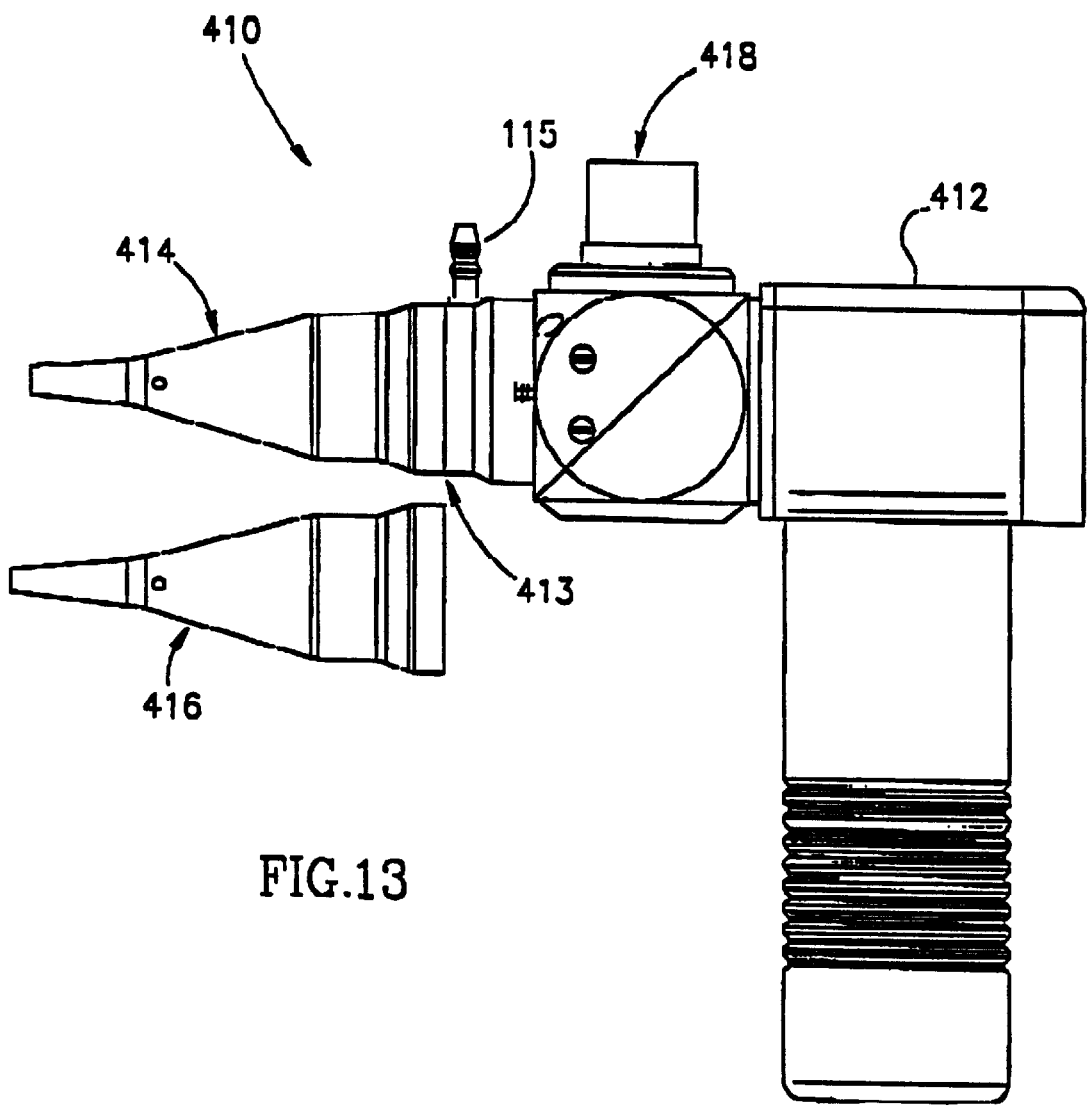
FIG. 13 is a schematic side view illustrating an otoscope adapted for use with a variety of different specula, in accordance with still another preferred embodiment of the present invention.

Reference is now made to FIG. 13 which is a schematic side view illustrating an otoscope adapted for use with a variety of different specula, in accordance with still another preferred embodiment of the present invention.

The otoscope 410 is different from the otoscopes whose optical layouts are illustrated in FIGS. 6, 11 and 12 in that it does not include the focusing assembly 150 disclosed hereinabove (FIG. 8). Instead, the otoscope 410 has a housing 412 having a fixed end 413 to which a speculum 414 is detachably attached. The speculum 414 is similar to the speculum 114 but may have different dimensions. The speculum 414 can be detached from the fixed end 413 and may be interchanged with any selected speculum chosen from a plurality of different specula. One such exemplary speculum 416 having different dimensions from the dimensions of the speculum 414 is shown in FIG. 13, detached from the otoscope 410.

Thus, the focusing of the laser beams may be achieved in the otoscope 410 by selecting a suitable speculum from a plurality of available differently sized specula (not shown) and attaching it to the fixed end 413 of the otoscope 410.

It is noted that when a flashscanner is used to perform myringotomy with a suitable otoscope of the present invention the surgical laser is preferably a continuous wave $CO_2$ laser, and the laser spot size used for perforating the tympanic membrane are approximately 1–mm in diameter. The exposure times using the flashscanner are approximately 0.05–0.2 seconds and the power levels used are in the range of approximately 10–20 Watts.

When a pulsed surgical laser such as a model 40C SHARPLAN $CO_2$ laser commercially available from Laser Industries Ltd., Israel is used, the spot size is approximately 0.3 mm at typical power levels of approximately 0.8–1.0 watts in the super-pulsed mode of the laser. In this operating mode the operator will need to repeatedly perforate the tympanic membrane at different locations until a roughly circular opening of approximately 1–3 mm in diameter is achieved.

When a pulsed Erbium surgical laser is used the spot size is approximately 1 to 3 mm at typical energy levels of approximately 0.3 to 1.0 joule, respectively.

While carrying out the laser surgery, it may be medically important to know when the tympanic membrane has been penetrated. As soon as this is known, the lasing process can cease to save the posterior section of the middle ear from unnecessary laser radiation (although the laser beam is expected to be unfocussed and not damaging).

Upon observation of the image 140 as seen on the display 72, the physician can watch the lasing of the hole through the membrane to know when the tympanic membrane of the ear drum has been penetrated to permit the escape of excess fluid. When such penetration arises, there will be a noticeable change in the observed characteristics at the target area as it appears on the display 72.

Electromagnetic radiation emissions from the target area in the tympanic membrane resulting from use of the surgical laser beam vary depending upon whether the tympanic membrane has been penetrated or not. The electromagnetic radiation emissions may be in the visible range, infra-red range or any range useful for sensing the penetration of the tympanic membrane.

For example, If a visible pilot laser beam is used to check the hole penetration, such as that from a He—Ne pilot laser, the reflected power level of the beam varies depending upon whether the tympanic membrane has been penetrated or not. In either case, penetration is readily observed on the display 72.

It is noted that, as an alternative to visually observing for changes on the display 72 to check penetration, the apparatus may include an automatic system for sensing the penetration of the tympanic membrane and automatically shutting off the lasing of the surgical laser upon detecting the penetration of the membrane.

Figure 14:
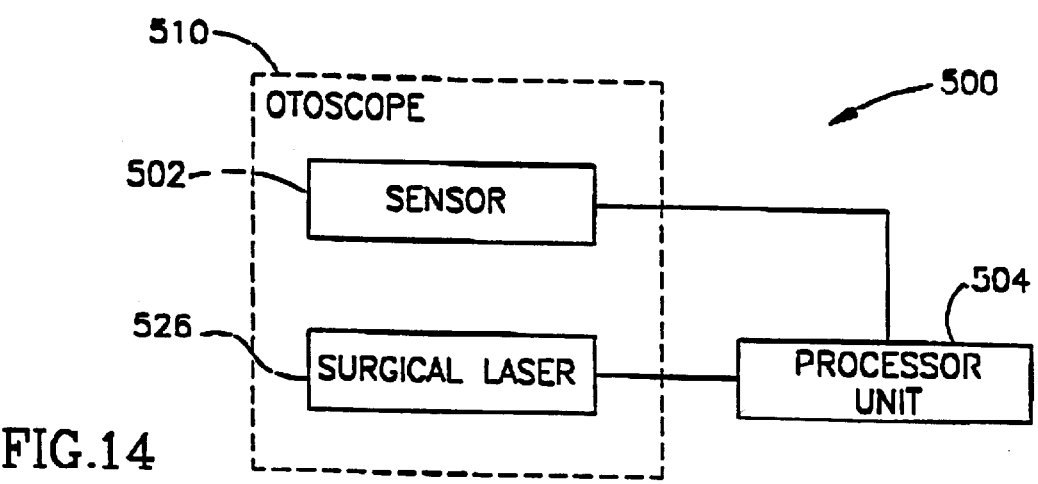
FIG. 14 is a schematic block diagram illustrating an automatic system for sensing the penetration of the tympanic membrane and for automatically shutting off the lasing of a surgical laser upon detecting penetration of the tympanic membrane, useful in a system for performing myringotomy with a focusable imaging laser otoscope, in accordance with another preferred embodiment of the present invention.

Reference is now made to FIG. 14 which is a schematic block diagram illustrating an automatic system for sensing the penetration of the tympanic membrane and for automatically shutting off the lasing of a surgical laser upon detecting penetration of the tympanic membrane, useful in a system for performing myringotomy with a focusable imaging laser otoscope, in accordance with another preferred embodiment of the present invention.

The system 500 includes a sensor 502 which is suitably attached within an otoscope 510 as disclosed in detail hereinabove. The otoscope 510 may be any of the otoscopes 110 and 410 of FIGS. 5 and 13, respectively, or another similarly designed otoscope. The system 500 further includes a processing unit 504 suitably connected to the sensor 502 for sensing changes in the level of electromagnetic radiation emissions from the target area in the tympanic membrane as disclosed in detail hereinabove. The processing unit 504 is further connected to the surgical laser 526 for controlling the lasing thereof. The processing unit 504 may include a microprocessor (not shown), a computer (not shown) or a dedicated micro-controller (not shown). The processing unit 504 may also include a data acquisition unit (not shown) for acquiring signal data from the sensor 502 prior to processing the signal.

It is noted that, for the sake of clarity of illustration, other components which may be included in the otoscope 510 such as the imaging device, the optical and mechanical assemblies and a pilot laser, are not shown in FIG. 14.

The sensor 502 may be positioned in the path (not shown) traveled by the reflected surgical laser beam or the reflected pilot laser beam. The sensor 502 may also be positioned to receive a portion of the reflected surgical laser beam or the reflected pilot laser beam which portion is split from the reflected surgical laser beam or the reflected pilot laser beam by a suitable optical element (not shown) such as a beam splitter, a mirror or any other suitable optical element. For instance, a sensor of reflected power level in the visible range could be used where a He—Ne pilot laser (not shown in FIG. 14) is used to illuminate the target during penetration of the tympanic membrane. Alternatively, the sensor 502 may be a sensor of infrared radiation emissions for use in conjunction with the surgical laser 526 which is used for performing the laser surgery. For example, the surgical laser 526 may be a $CO_2$ laser which is fired at the target area on the tympanic membrane resulting in reflection of infra-red radiation from the target area. The intensity of the reflected infra-red radiation is sensed by the infra-red sensor. Penetration of the tympanic membrane target area forming a hole in the membrane is accompanied by a reduction of the intensity of infra-red light reflected from the target area.

The sensor 502 senses the intensity of radiation reflected from the target area to produce a signal such as a voltage signal, a current signal or any other suitable signal which is proportional to the intensity of the reflected radiation and feeds the signal to the processing unit 504. The processing unit 504 processes the signal to determine whether penetration of the tympanic membrane has occurred. If the processing unit 504 determines that penetration has occurred, it will send a signal to the surgical laser 526 to shut off the lasing, preventing further lasing after penetration and reducing the possibility of damage to the middle ear.

One exemplary method for determining if penetration has occurred includes comparing the intensity of the signal to a threshold value. If the signal value is less than the threshold value, the processing unit terminates the lasing of the surgical laser 526. The threshold value can be a predetermined value. Alternatively, the threshold value can be dynamically determined as a fraction of the intensity signal sampled and averaged over a predetermined time period prior to penetration of the tympanic membrane.

Other methods suitable for determining if penetration has occurred based on processing of the reflected radiation signal of the sensor 502 are known in the art. Such methods will therefore not be discussed in detail hereinafter.

The present invention could also be used on adults or animals.

In addition, the present invention has application to other forms of treatment in the ear other than for treating myringotomy and may be directed at other regions of the ear other than the tympanic membrane. The present invention has application for treatment of the eye, mouth, nose, skin and other parts of the head where the risk of unexpected, sudden head movement during laser surgery is detrimental. Indeed, the present inventive apparatus may be used to treat any external part of the body.

While the foregoing description and drawings represent the preferred embodiments of the present invention, it will be understood that various changes and modifications may be made which are within the scope and spirit of the present invention.

What is claimed is:

1. An apparatus for performing laser surgery without the need for anesthesia, comprising:

a housing having an end;

an imaging device attached to said housing for producing an image of a target area;

an illuminating system attached to said housing for illuminating said target area;

a speculum having a longitudinal axis, a first end and a second end, said second end of said speculum detachably attached to said end of said housing; and, an optical system attached to said housing and having a main optical axis substantially coaxial with said longitudinal axis of said speculum, for directing at least one energy beam emitted from a laser source through said housing and said speculum to strike said target area and for directing image forming light rays to project an image of said target area onto said imaging device such that when said image of said target area is focused, said at least one energy beam is also focused on said target area.

2. The apparatus according to claim 1 wherein said speculum is exchangeable with any selected one of a plurality of specula, each one of said plurality of specula having different dimensions, and wherein said image of said target area is focused by selecting a suitable speculum out of said plurality of specula.

3. The apparatus according to claim 1 additionally comprising:
laser source for generating said at least one energy beam.

4. The apparatus according to claim 3, additionally comprising a scanner, wherein said laser source is connected to said housing through said scanner for scanning said at least one energy beam along a portion of said target area.

5. The apparatus according to claim 4, wherein said scanner is selected from the group comprising: a flashscanner and a silktouch scanner.

6. The apparatus according to claim 3, wherein said laser source for generating said at least one energy beam is configured for generating at least two energy beams, the first energy beam consisting of a surgical laser beam and the second energy beam consisting of an aiming laser beam.

7. The apparatus according to claim 6, wherein said illuminating system includes a non coherent light source coupled to an optical fiber bundle for providing an illuminating beam directed towards said target area.

8. The apparatus according to claim 7, wherein said optical system includes a dichroic beam combiner and a beam splitter for combining said surgical laser beam and/or said aiming laser beam with viewing rays directed by said optical system towards said imaging device and with said illuminating beam.

9. The apparatus according to claim 6, wherein said aiming laser beam is produced by an aiming laser source attached within said housing.

10. The apparatus according to claim 9 wherein said aiming laser source includes an aiming laser and coupling optics for combining said aiming laser beam with said surgical laser beam.

11. The apparatus according to claim 10 wherein said aiming laser is a diode laser.

12. The apparatus according to claim 6, wherein said laser source includes a pulsed or a continuous laser.

13. The apparatus according to claim 12 wherein said laser source further includes an aiming laser.

14. The apparatus according to claim 6, wherein said laser source includes a surgical laser coupled to said optical system by an optical fiber.

15. The apparatus according to claim 14 wherein said surgical laser is selected from the group comprising: a pulsed laser and a continuous wave laser.

16. The apparatus according to claim 14 wherein said surgical laser is selected from the group comprising: pulsed $CO_2$ laser, a continuous $CO_2$ laser and an erbium laser.

17. The apparatus according to claim 14 wherein said aiming laser beam is produced by an aiming laser source attached within said housing, said aiming laser source includes an aiming laser and coupling optics for combining said aiming laser beam with said surgical laser beam and wherein said optical system includes a dichroic beam combiner for combining said surgical laser beam and said aiming laser beam with said image forming light rays.

18. The apparatus according to claim 6, wherein said surgical laser beam has a power level and reflects off the desired target area, said apparatus further includes a sensor arranged in a path traveled by the reflected surgical laser beam said sensor detects changes in the power level reflected off the desired target area, said sensor indicating when the power level being reflected is such that the penetration of said desired target area has occurred.

19. The apparatus according to claim 6, wherein electromagnetic radiation emissions emanate from said target area in response to said surgical laser beam or said aiming laser beam striking said target area, said apparatus further includes a sensor arranged in a path traveled by said electromagnetic radiation emissions, said sensor detects changes in said electromagnetic radiation emissions from said target area, said sensor indicating when said electromagnetic radiation emissions are such that penetration of said target area has occurred.

20. The apparatus according to claim 19, wherein said sensor is connected to a processing unit, said processing unit is connected to said laser source for controlling the operation thereof, said processing unit determines from signals produced by said sensor whether penetration of said target has occurred, said processing unit automatically shuts off said surgical laser beam after penetration of said target has occurred.

21. The apparatus according to claim 1 wherein said illuminating system includes a non coherent light source coupled to an optical fiber bundle for providing an illuminating beam directed towards said target area.

22. The apparatus according to claim 1 wherein said illuminating system includes a non coherent light source, an illuminating member attached to said housing and an optical fiber bundle, said optical fiber bundle having a first end optically coupled to said non-coherent light source and a second end disposed within said illuminating member to provide an annular illuminating source at an end of said illuminating member facing said target area.

23. The apparatus according to claim 1 wherein said imaging device is a charge coupled device or a video camera.

24. The apparatus according to claim 1 further including a display device for displaying said image of said target area to a user.

25. An apparatus for performing laser surgery without the need for anesthesia, comprising:
a housing;
an imaging device attached to said housing for producing an image of a target area;
an illuminating system for illuminating said target area attached to said housing;
a speculum having a longitudinal axis, a first end and a second end, said second end of said speculum detachably and movably attached to said housing;
an optical system attached to said housing and having a main optical axis substantially coaxial with said longitudinal axis of said speculum, for directing at least one energy beam emitted from a laser source through said housing and said speculum to strike said target area and for directing image forming light rays to project an image of said target area onto said imaging device such that when said image of said target area is focused, said at least one energy beam is also focused on said target area; and
a focusing mechanism attached to said speculum for adjustably moving said speculum relative to said housing along said main optical axis to focus said image of said target area.

26. The apparatus according to claim 25, additionally comprising a laser source for generating said at least one energy beam.

27. The apparatus according to claim 26, wherein said laser source for generating said at least one energy beam is configured for generating at least two energy beams, the first energy beam consisting of a surgical laser beam and the second energy beam consisting of an aiming laser beam.

28. The apparatus according to claim 27, wherein said surgical laser beam has a power level and reflects off said target area, said apparatus further includes a sensor arranged in a path traveled by the reflected surgical laser beam, said sensor detects changes in the power level reflected off said target area, said sensor indicating when the power level being reflected is such that the penetration of said target area has occurred.

29. The apparatus according to claim 27, wherein electromagnetic radiation emissions emanate from said target area in response to said surgical laser beam or said aiming laser beam striking said target area, said apparatus further includes a sensor arranged in a path traveled by said electromagnetic radiation emissions, said sensor detects changes in said electromagnetic radiation emissions from said target area, said sensor indicating when said electromagnetic radiation emissions are such that the penetration of said target area has occurred.

30. The apparatus according to claim 29, wherein said sensor is connected to a processing unit, said processing unit is connected to said laser source for controlling the operation thereof, said processing unit determines from signals produced by said sensor whether penetration of said target has occurred, said processing unit automatically shuts off said surgical laser beam after penetration of said target has occurred.

31. An apparatus for performing laser surgery without the need for anesthesia, comprising:
 a housing;
 an end member movably disposed within said housing;
 an imaging device attached to said housing for producing an image of a target area;
 an illuminating system attached to said housing for illuminating said target area;
 a speculum having a longitudinal axis, a first end and a second end, said second end or said speculum detachably attached to said end member;
 an optical system attached to said housing and having a main optical axis substantially coaxial with said longitudinal axis of said speculum, for directing at least one energy beam emitted from a laser source through said housing and said speculum to strike said target area and for directing image forming light rays to project an image of said target area onto said imaging device such that when said image of said target area is focused, said at least one energy beam is also focused on said target area; and
 a focusing assembly attached to said housing and to said end member for adjustably moving said end member and said speculum relative to said housing to focus said image of said target area.

32. The apparatus according to claim 1, additionally comprising;
 a laser source for generating said at least one energy beam.

33. The apparatus according to claim 32, additionally comprising a scanner, wherein said laser source is connected to said housing through said scanner for scanning said at least one energy beam along a portion of said target area.

34. The apparatus according to claim 33, wherein said scanner is selected from the group comprising: a flashscanner and a silktouch scanner.

35. The apparatus according to claim 32, wherein said laser source for generating said at least one energy beam is configured for generating at least two energy beams, the first energy beam consisting of a surgical laser beam and the second energy beam consisting of an aiming laser beam.

36. The apparatus according to claim 35, wherein said illuminating system comprises a non coherent light source coupled to an optical fiber bundle for providing an illuminating beam directed towards said target area.

37. The apparatus according to claim 36, wherein said optical system comprises a dichroic beam combiner and a beam splitter for combining said surgical laser beam and said aiming laser beam with viewing rays directed by said optical system towards said imaging device and with said illuminating beam.

38. The apparatus according to claim 35, wherein said laser source includes a pulsed or a continuous laser.

39. The apparatus according to claim 38 wherein said laser source further includes an aiming laser.

40. The apparatus according to claim 35, wherein said laser source includes a surgical laser coupled to said optical system by an optical fiber.

41. The apparatus according to claim 40 wherein said surgical laser is selected from the group comprising: a pulsed laser and a continuous wave laser.

42. The apparatus according to claim 40 wherein said surgical laser is selected from the group comprising: a pulsed $CO_2$ laser, a continuous $CO_2$ laser and an erbium laser.

43. The apparatus according to claim 40 wherein said aiming laser beam is produced by an aiming laser source attached within said housing, said aiming laser source comprises an aiming laser and coupling optics for combining said aiming laser beam with said surgical laser beam and wherein said optical system includes a dichroic beam combiner for combining said surgical laser beam and said aiming laser beam with said image forming light rays.

44. The apparatus according to claim 35, wherein said aiming laser beam is produced by an aiming laser source attached within said housing.

45. The apparatus according to claim 44 wherein said aiming laser source comprises an aiming laser and coupling optics for combining said aiming laser beam with said surgical laser beam.

46. The apparatus according to claim 45 wherein said aiming laser is a diode laser.

47. The apparatus according to claim 35, wherein said surgical laser beam has a power level and reflects off the desired target area, said apparatus further includes a sensor arranged in a path traveled by the reflected surgical laser beam said sensor detects changes in the power level reflected off the desired target area, said sensor indicating when the power level being reflected is such that the penetration of the desired target area has occurred.

48. The apparatus according to claim 35, wherein electromagnetic radiation emissions emanate from said target area in response to said surgical laser beam or said aiming laser beam striking said target area, said apparatus further includes a sensor arranged in a path traveled by said electromagnetic radiation emissions, said sensor detects changes in said electromagnetic radiation emissions from said target area, said sensor indicating when said electromagnetic emissions are such that penetration of said target area has occurred.

49. The apparatus according to claim 48, wherein said sensor is connected to a processing unit, said processing unit is connected to said laser source for controlling the operation thereof, said processing unit determines from signals produced by said sensor whether penetration of said target has occurred, said processing unit automatically shuts off said surgical laser beam after penetration of said target has occurred.

50. The apparatus according to claim 31 wherein said illuminating system comprises a non coherent light source coupled to an optical fiber bundle for providing an illuminating beam directed towards said target area.

51. The apparatus according to claim 31 wherein said illuminating system comprises a non coherent light source, an illuminating member attached to said housing and an optical fiber bundle, said optical fiber bundle having a first end optically coupled to said non-coherent light source and a second end disposed within said illuminating member to provide an annular illuminating source at an end of said illuminating member facing said target area.

52. The apparatus according to claim 31 wherein said imaging device is a charge coupled device or a video camera.

53. The apparatus according to claim 31 further comprising a display device for displaying said image of said target area to a user.

54. A method for performing laser myringotomy without the need for anesthesia, using a focusable imaging laser otoscope including a housing, a speculum movable with respect to the housing, an illuminating system attached to the housing for illuminating a target area, a surgical laser source and an aiming laser source connected to the housing, an optical system and an imaging device attached to the housing for imaging the target area, said otoscope being connected to a display connected to the imaging device, the method comprising the steps of:

inserting said speculum into the opening of an ear;

displaying an image indicative of said target area on said display;

focusing said image of said target area on said display by moving said speculum relative to said housing;

directing an aiming laser beam produced by said aiming laser source towards a desired portion of said target area suitable for performing laser surgery, to form an illuminated aiming spot on said desired portion, said spot being visible within said image displayed on said display;

adjusting the position of said spot on said desired portion of said target area by suitably moving said otoscope within said ear; and firing a surgical laser beam produced by said surgical laser source towards said desired portion of said target area.

55. The method according to claim 54 wherein said target area is the tympanic membrane of the eardrum of said ear and said image is indicative of said tympanic membrane.

56. The method according to claim 54, wherein said surgical laser beam has a power level and reflects of said desired portion, said otoscope further includes a sensor arranged in a path traveled by the reflected surgical laser beam, said sensor detects changes in the power level reflected off said desired portion, the method further includes the step of, indicating when the power level being reflected is such that the penetration of said desired portion of said target area has occurred.

57. The method according to claim 54, wherein electromagnetic radiation emissions emanate from said desired portion of said target area in response to said surgical laser beam or said aiming laser beam striking said desired portion, said apparatus further includes a sensor arranged in a path traveled by said electromagnetic radiation emissions, said sensor detects changes in said electromagnetic radiation emissions from said desired portion, the method further includes the step of, indicating when said electromagnetic radiation emissions are such that the penetration of said desired portion of said target area has occurred.

58. The method according to claim 57, wherein said sensor is connected to a processing unit, said processing unit is connected to said surgical laser source for controlling the operation thereof, the method further includes after the step of firing a surgical laser beam, the steps of, said processing unit determining from signals produced by said sensor whether penetration of said target has occurred; and automatically shutting off said surgical laser beam by said processing unit after penetration of said target has occurred.

59. A method for performing laser myringotomy without the need for anesthesia, using an imaging laser otoscope including a housing, a speculum detachably attached to the housing, an illuminating system attached to the housing for illuminating a target area, a surgical laser source and an aiming laser source connected to the housing, an optical system and an imaging device attached to the housing for imaging the target area, the otoscope is connected to a display connected to the imaging device, the method comprising the steps of:

selecting said speculum from a plurality of specula having different dimensions;

attaching said speculum to said housing;

inserting said speculum into the opening of an ear;

displaying an image indicative of said target area on said display;

focusing said image of said target area on said display by moving said speculum within said ear;

directing an aiming laser beam produced by said aiming laser source towards a desired portion of said target area suitable for performing laser surgery, to form an illuminated aiming spot on said desired portion, said spot being visible within said image displayed on said display;

adjusting the position of said spot on said desired portion of said target area by suitably moving said otoscope within said ear; and firing a surgical laser beam produced by said surgical laser source towards said desired portion of said target area.

60. The method according to claim 59 wherein said target area is the tympanic membrane of the eardrum of said ear and said image is indicative of said tympanic membrane.

61. The method according to claim 59 wherein said surgical laser beam has a power level and reflects of said desired portion, said otoscope further includes a sensor arranged in a path traveled by the reflected surgical laser beam, said sensor detects changes in the power level reflected off said desired portion, the method further includes the step of, indicating when the power level being reflected is such that the penetration of said desired portion of said target area has occurred.

62. The method according to claim 59, wherein electromagnetic radiation emissions emanate from said desired portion of said target area in response to said surgical laser beam or said aiming laser beam striking said desired portion, said apparatus further includes a sensor arranged in a path traveled by said electromagnetic radiation emissions, said sensor detects changes in said electromagnetic radiation emissions from said desired portion, the method further includes the step of, indicating when said electromagnetic radiation emissions are such that the penetration of said desired portion of said target area has occurred.

63. The method according to claim 62, wherein said sensor is connected to a processing unit, said processing unit is connected to said surgical laser source for controlling the operation thereof, the method further includes after the step of firing a surgical laser beam, the steps of, said processing unit determining from signals produced by said sensor whether penetration of said target has occurred; and automatically shutting off said surgical laser beam by said processing unit after penetration of said target has occurred.

* * * * *